US010301263B2

(12) United States Patent
Williams et al.

(10) Patent No.: US 10,301,263 B2
(45) Date of Patent: May 28, 2019

(54) ANTICONVULSANT COMPOUND

(71) Applicant: Royal Holloway and Bedford New College, Egham, Surrey (GB)

(72) Inventors: Robin Williams, Egham (GB); Matthew Walker, London (GB)

(73) Assignee: Royal Holloway and Bedford New College, Egham, Surrey (GB)

( * ) Notice: Subject to any disclaimer, the term of this patent is extended or adjusted under 35 U.S.C. 154(b) by 0 days.

(21) Appl. No.: 15/509,772

(22) PCT Filed: Sep. 10, 2015

(86) PCT No.: PCT/GB2015/052624
§ 371 (c)(1),
(2) Date: Mar. 8, 2017

(87) PCT Pub. No.: WO2016/038379
PCT Pub. Date: Mar. 17, 2016

(65) Prior Publication Data
US 2017/0305859 A1    Oct. 26, 2017

(30) Foreign Application Priority Data

Sep. 10, 2014  (GB) .................................. 1416017.0

(51) Int. Cl.
| | |
|---|---|
| *C07C 61/08* | (2006.01) |
| *A61K 31/19* | (2006.01) |
| *A61P 25/08* | (2006.01) |
| *C07D 211/60* | (2006.01) |
| *A61K 31/13* | (2006.01) |
| *A61K 31/136* | (2006.01) |
| *A61K 31/137* | (2006.01) |
| *A61K 31/16* | (2006.01) |
| *A61K 31/165* | (2006.01) |
| *A61K 31/166* | (2006.01) |
| *A61K 31/192* | (2006.01) |
| *A61K 31/195* | (2006.01) |
| *A61K 31/445* | (2006.01) |
| *C07C 53/134* | (2006.01) |
| *C07C 59/13* | (2006.01) |
| *C07C 61/35* | (2006.01) |
| *C07C 62/10* | (2006.01) |
| *C07C 61/09* | (2006.01) |
| *C07C 229/28* | (2006.01) |

(52) U.S. Cl.
CPC ............ *C07D 211/60* (2013.01); *A61K 31/13* (2013.01); *A61K 31/136* (2013.01); *A61K 31/137* (2013.01); *A61K 31/16* (2013.01); *A61K 31/165* (2013.01); *A61K 31/166* (2013.01); *A61K 31/19* (2013.01); *A61K 31/192* (2013.01); *A61K 31/195* (2013.01); *A61K 31/445* (2013.01); *A61P 25/08* (2018.01); *C07C 53/134* (2013.01); *C07C 59/13* (2013.01); *C07C 61/08* (2013.01); *C07C 61/09* (2013.01); *C07C 61/35* (2013.01); *C07C 62/10* (2013.01); *C07C 229/28* (2013.01); *C07C 2601/14* (2017.05)

(58) Field of Classification Search
CPC .......... C07C 61/08; A61K 31/19; A61P 25/08
USPC .................. 562/400, 507, 508, 510; 514/557
See application file for complete search history.

(56) References Cited

U.S. PATENT DOCUMENTS

| 4,283,420 A | * | 8/1981 | Pigerol | .................. C07C 51/08 514/557 |
|---|---|---|---|---|
| 2002/0068692 A1 | | 6/2002 | Willis | |
| 2004/2009858 | | 10/2004 | Bennani et al. | |

FOREIGN PATENT DOCUMENTS

| JP | 2004123558 | 4/2004 |
|---|---|---|
| WO | 1998020864 | 5/1998 |
| WO | 2005079300 | 9/2005 |
| WO | 2005084654 | 9/2005 |
| WO | 2006012603 | 2/2006 |
| WO | 2006097744 | 9/2006 |
| WO | 2007112288 | 10/2007 |
| WO | 2007119108 | 10/2007 |
| WO | 2008005407 | 1/2008 |
| WO | 2010127440 | 11/2010 |
| WO | 2014185561 | 11/2014 |

OTHER PUBLICATIONS

Patsalos, P.N., Epilepsia, 56(1):12-27, 2015.*
Cecil Textbook of Medicine, edited by Bennet, J.C., and Plum F., 20th edition,vol. 1, 1004-1010, 1996.*
Dermeret al., Bio/Technology, 1994, 12:320.*
Freshney et al.,Culture of Animal Cells, A Manual of Basic Technique, Alan R. Liss, Inc., 1983, New York, p. 4.*
pccompound selected 1-200, Create Date Mar. 26, 2005 to Nov. 30, 2012.*
pccompound selected 201-276, Create Date Nov. 30, 2012 to Mar. 24, 214.*
pccompound-selected items 1-200 of 14832, Create Date Mar. 25, 2005 to Jan. 6, 2014.*
pccompound 1-200 of 276 , Create Date Mar. 26, 2005 to Nov. 30, 2012.*

(Continued)

*Primary Examiner* — Venkataraman Balasubramanian
(74) *Attorney, Agent, or Firm* — Rudy J. Ng; Bozicevic, Field & Francis LLP

(57) ABSTRACT

The invention relates to pharmaceutical uses of compounds of formula (II). Particular aspects of the invention relate to the use of those compounds in treating, preventing or ameliorating a seizure-related disorder, bipolar disorder, mania, migraine, Alzheimer's disease, Parkinson's disease or stroke.

13 Claims, 8 Drawing Sheets

(56) References Cited

OTHER PUBLICATIONS pccompound selected items 1-62, Create Date Mar. 26, 2005 to Dec. 1, 2012.*
Moosman et al., (2001) "Protective Activity of Aromatic Amines and Imines Against Oxidative Nerve Cell Death," Biological Chemistry, Walter De Gruyter GMBH & CO 382(11) 1601-1612.
Database Registry (1984) "Cyclohexanecarboxylic acid, 4-(2-methylbutyl)-" Database accession No. 62614-49-7 p. 1 XP-002750564.
Database Registry (1984) "Cyclohexaneacetic acid, 4-(4-methylpentyl)-" Chemical Abstracts Service, Columbus, Ohio, US Database accession No. 74603-20-6 p. 1 XP-002750565.
Database Registry "Cyclohexanecarboxylic acid, 4-(1-butenyl)-, [1.alpha.,4.beta.(E)]" Database accession No. 105558-46-1 p. XP-002750566.
Database Registry (2007) "Cyclohexanecarboxylic acid, 4-propoxy-" Database accession No. 950772-21-1 p. 1 XP-002750567.
Database Registry (2010) "Cyclohexanecarboxylic acid, 4-(ethoxymethyl)-" Database accession No. 1254114-34-5 p. 1 XP-002750568.
Database Registry (2011) "Cyclohexanecarboxylic acid, 4-(3-methylbutyl)-" Database accession No. 1309126-93-9 p. 1 XP-002750569.
Wallenstein (1987) "Attenuation of Penicillin Models of Epilepsy by Nonsteroidal Anti-inflammatory Drugs," Experimental Neurology 98, 152-160.

* cited by examiner

Figure 5

| Compound | Species | Seizure model | dose (mg/kg) | animals (protected/tested) | animals (Toxic/tested) | ED$_{50}$ (mg/kg) |
|---|---|---|---|---|---|---|
| 4-BCCA[a] | Mice | 6Hz | 100 | 3/4 | 0/4 | 81 |
| | Rat | MES | 100 | 4/8 | 1/8[†] | ~100* |
| | Mice | scMET | 150 | 4/8 | 0/8 | ~150* |
| | Mice | CKM | 80 | 8/8 | 0/8 | 44 |
| VPA | Mice | 6Hz | | | | 263[b] |
| | Rat | MES | | | | 485[c] |
| | Mice | scMET | | | | 191[d] |
| | Mice | CKM | | | | 174[e] |

ANTICONVULSANT COMPOUND

CROSS-REFERENCE TO RELATED APPLICATIONS

This application is the U.S. national phase under 35 U.S.C. § 371 of PCT International Application No. PCT/GB2015/052624, which has an international filing date of Sep. 10, 2015 and designated the United States of America, which application claims benefit of priority to GB Application No. 1416017.0, filed Sep. 10, 2014, the disclosures of each of which are incorporated by reference herein.

The present invention relates to anticonvulsant compounds for use in treating a range of diseases, such as seizure-related disorders, bipolar disorders, mania, migraine, Alzheimer's disease, Parkinson's disease or stroke. The invention extends to pharmaceutical compositions and method of treating such diseases.

Epilepsy is a common and severe neurological condition affecting up to 0.5-1% of the population worldwide. Despite the development of a range of new anti-epileptic drugs giving rise to improved tolerability, reduced side effects, and reduced interaction potential, around 30% of diagnosed patients continue to experience seizures. The development of new treatments for drug resistant epilepsy therefore addresses a major unmet need.

In an alternative approach to drug treatment, a specialized diet has proven successful in seizure control in people with severe, drug resistant epilepsy, specifically in children. This medium chain triglyceride (MCT) ketogenic diet, first introduced in 1971, was based around a reduction in dietary carbohydrate and an increase in medium chain fatty acid intake, in the form of triglycerides containing 81% octanoic acid and 16% decanoic acid. This diet gives rise to elevated blood levels of octanoic acid and decanoic acid. Recent data have suggested that, although octanoic acid does not directly control seizures, specific branched derivatives of octanoic acid provide more potent seizure control than a commonly used anti-epileptic drug, valproic acid, a congener of octanoic acid. Development of these branched chain fatty acids may therefore provide an alternative to the diet by overcoming the poor tolerability and metabolic consequences of the diet, especially in adults, that lead to poor compliance.

Since the MCT ketogenic diet and valproic acid show a range of therapeutic indications, improved therapies may be developed for treating seizure-related disorders, bipolar disorders, mania, migraine, Alzheimer's disease, Parkinson's disease or stroke.

The inventors have identified a new family of compounds, and they have shown that these compounds exhibit surprising inhibitory activity of the key excitatory neurotransmitter receptor, AMPA. Inhibition of AMPA is a well-described mechanism for seizure control, and the inventors further show that compounds within this family provide potent seizure control treatments in multiple seizure models. This study therefore identifies a novel family of compounds, with a defined cyclic structure, that shows promise as new treatments for the control of seizure-related disorders, bipolar disorders, mania, migraine, Alzheimer's disease, Parkinson's disease or stroke.

In a first aspect, there is provided a compound of formula (II):

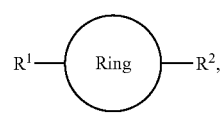

Formula (II)

wherein:
$R^1$ is a carboxylic acid, amide or amine;
Ring is selected from one of formulae (i) to (xi):

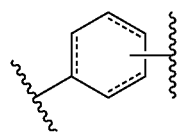
(i)

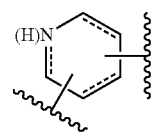
(ii)

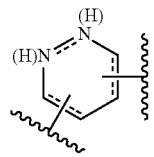
(iii)

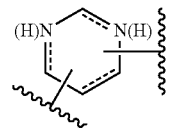
(iv)

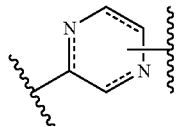
(v)

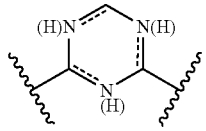
(vi)

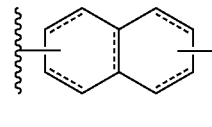
(vii)

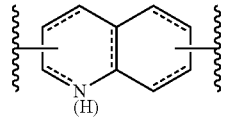
(viii)

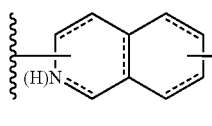
(ix)

-continued

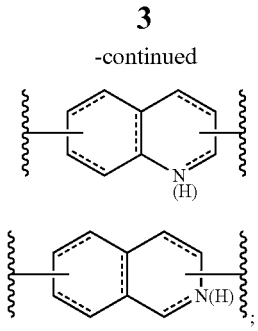
(x)

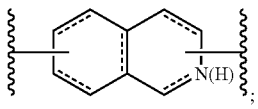
(xi)

and

R² is an optionally substituted straight or branched alkyl or alkenyl group with 1 to 20 C atoms, and wherein the backbone of the alkyl or alkenyl group is optionally interrupted by one or more heteroatoms; or a functional analogue, pharmaceutically acceptable salt or solvate thereof, for use in therapy or as a medicament.

While the present invention has resulted from the inventor's work in looking for compounds which could effectively treat epilepsy, it will be understood that targeting AMPA will allow treatment of diseases that also work by similar mechanisms, including seizure-related disorders, bipolar disorders, mania, migraine, Alzheimer's disease, Parkinson's disease or stroke.

Accordingly, in a second aspect, there is provided a compound of formula (II):

Formula (II)

wherein
R¹ is a carboxylic acid, amide or amine;
Ring is selected from one of formulae (i) to (xi):

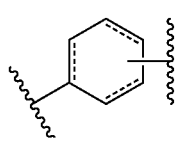
(i)

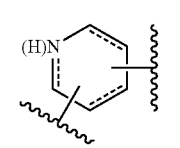
(ii)

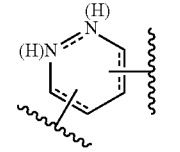
(iii)

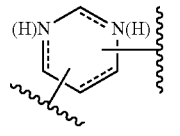
(iv)

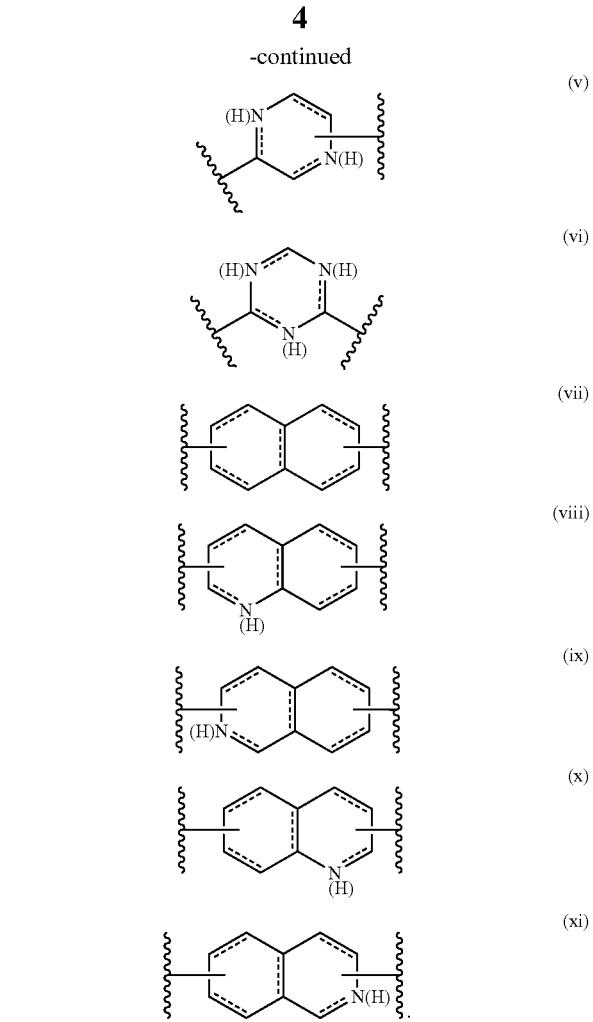

and

R² is an optionally substituted straight or branched alkyl or alkenyl group with 1 to 20 C atoms, and wherein the backbone of the alkyl or alkenyl group is optionally interrupted by one or more heteroatoms; for use in treating, preventing or ameliorating a seizure-related disorder, bipolar disorder, mania, migraine, Alzheimer's disease, Parkinson's disease or stroke.

In a third aspect, there is provided a method of treating, preventing or ameliorating a seizure-related disorder, bipolar disorder, mania, migraine, Alzheimer's disease, Parkinson's disease or stroke, the method comprising administering, to a subject in need of such treatment, a therapeutically effective amount of the compound as previously defined, or a functional analogue, pharmaceutically acceptable salt or solvate thereof.

Preferably, the compound is for use in treating, preventing or ameliorating a seizure-related disorder, more preferably epilepsy, and most preferably drug resistant epilepsy.

Preferably, the compound is for use in inhibiting the α-amino-3-hydroxy-5-methyl-4-isoxazolepropionic acid (AMPA) receptor. More preferably, the compound is for use in inhibiting AMPA receptor GluA2/3 and/or GluA1/2.

In some embodiments the compound may comprise a compound of formula (I):

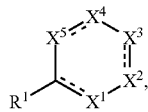

Formula (I)

wherein:
X¹ is $CHR^2$, $CR^2$, CH, $CH_2$, N or NH;
X² is $CHR^2$, $CR^2$, CH, $CH_2$, N or NH;
X³ is $CHR^2$, $CR^2$, CH, $CH_2$, N or NH;
X⁴ is $CHR^2$, $CR^2$, CH, $CH_2$, N or NH;
X⁵ is $CHR^2$, $CR^2$, CH, $CH_2$, N or NH; and
wherein one of X¹, X², X³, X⁴ and X⁵ is $CHR^2$ or $CR^2$.

Accordingly, the Ring referred to in Formula (II) may be selected from any one of formulae (i) to (vi).

In one preferred embodiment, the compound comprises a compound of formula (Ia):

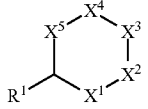

Formula (Ia)

wherein:
X¹ is $CHR^2$, $CH_2$ or NH;
X² is $CHR^2$, $CH_2$ or NH;
X³ is $CHR^2$, $CH_2$ or NH;
X⁴ is $CHR^2$, $CH_2$ or NH; and
X⁵ is $CHR^2$, $CH_2$ or NH;
and one of X¹, X², X³, X⁴ and X⁵ is $CHR^2$.

Accordingly, the Ring referred to in Formula (II) may be selected from any one of formulae (i-a) to (vi-a):

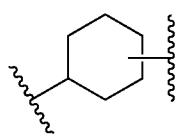

(i)

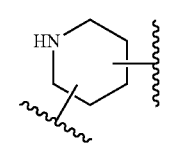

(ii)

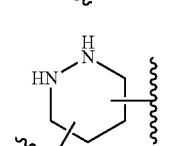

(iii)

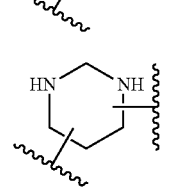

(iv)

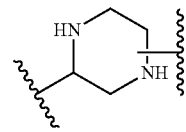

(v)

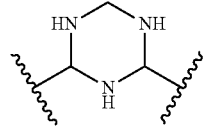

(vi)

In embodiments where the compound comprises a compound of formula (Ia), then R¹ and R² may be positioned in a cis-relationship to each other. Alternatively, R¹ and R² may be positioned in a trans-relationship to each other.

In an alternative preferred embodiment, the compound comprises a compound of formula (Ib):

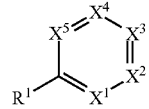

Formula (Ib)

wherein:
X¹ is $CR^2$, CH or N;
X² is $CR^2$, CH or N;
X³ is $CR^2$, CH or N;
X⁴ is $CR^2$, CH or N; and
X⁵ is $CR^2$, CH or N;
and one of X¹, X², X³, X⁴ and X⁵ is $CR^2$.

Accordingly, Ring referred to in Formula (II) may be selected from one of formulae (i-b) to (vi-b):

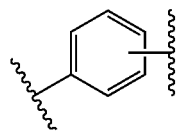

(i-b)

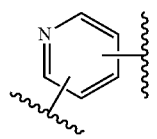

(ii-b)

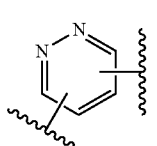

(iii-b)

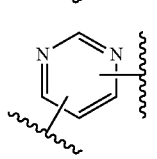

(iv-b)

-continued

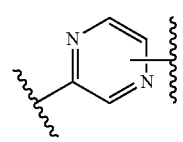
(v-b)

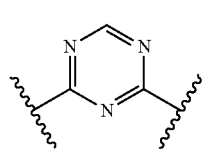
(vi-b)

In one preferred embodiment, the compound comprises a compound of formula (Ic):

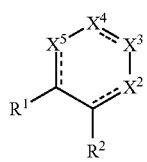
Formula (Ic)

wherein:
$X^2$ is CH, $CH_2$, N or NH;
$X^3$ is CH, $CH_2$, N or NH;
$X^4$ is CH, $CH_2$, N or NH; and
$X^5$ is CH, $CH_2$, N or NH.

Accordingly, the Ring referred to in Formula (II) may be selected from any one of formulae (i) to (v).

In a preferred embodiment, the compound comprises a compound of formula (Id):

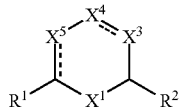
Formula (Id)

wherein:
$X^1$ is CH, $CH_2$, N or NH;
$X^3$ is CH, $CH_2$, N or NH;
$X^4$ is CH, $CH_2$, N or NH; and
$X^5$ is CH, $CH_2$, N or NH.

Accordingly, the Ring referred to in Formula (II) may be selected from any one of formulae (i) to (vi).

In a more preferred embodiment, the compound comprises a compound of formula (Ie):

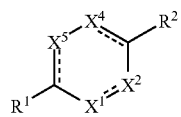
Formula (Ie)

wherein:
$X^1$ is CH, $CH_2$, N or NH;
$X^2$ is CH, $CH_2$, N or NH;
$X^4$ is CH, $CH_2$, N or NH; and
$X^5$ is CH, $CH_2$, N or NH.

Accordingly, the Ring referred to in Formula (II) may be selected from any one of formulae (i) to (v).

$R^1$ may be selected from a carboxylic acid, amide or amine group with 1 to 5 C atoms, preferably with 1 to 3 C atoms, more preferably with 1 to 2 C atoms. Preferably, $R^1$ is a carboxylic acid with 1 to 5 C atoms, preferably 1 to 3 C atoms, more preferably 1 to 2 C atoms. Preferably, $R^1$ comprises methanoic acid or ethanoic acid.

Accordingly, in a preferred embodiment, the compound comprises a compound of formula (If):

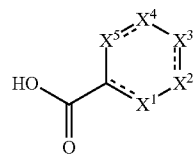
Formula (If)

In a further preferred embodiment, the compound comprises a compound of formula (Ig):

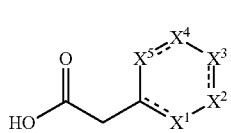
Formula (Ig)

It will be appreciated that the six-membered ring may comprise a substituted benzene ring. Accordingly, in one embodiment, the compound may comprise a compound of formula (Ih):

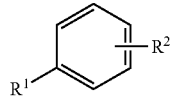
Formula Ih wherein:
$X^1$ is $CR^2$ or CH;
$X^2$ is $CR^2$ or CH;
$X^3$ is $CR^2$ or CH;
$X^4$ is $CR^2$ or CH; and
$X^5$ is $CR^2$ or CH;
and one of $X^1$, $X^2$, $X^3$, $X^4$ and $X^5$ is $CR^2$.

Accordingly, the Ring referred to in Formula (II) is formulae (i-b).

It will be appreciated that the six-membered ring may comprise a substituted cyclohexane ring. Accordingly, in one embodiment, the compound may comprise a compound of formula (Ii):

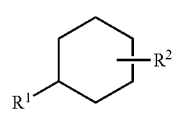
Formula Ii wherein:
$X^1$ is $CHR^2$ or $CH_2$;
$X^2$ is $CHR^2$ or $CH_2$;
$X^3$ is $CHR^2$ or $CH_2$;
$X^4$ is $CHR^2$ or $CH_2$; and
$X^5$ is $CHR^2$ or $CH_2$;
and one of $X^1$, $X^2$, $X^3$, $X^4$ and $X^5$ is $CHR^2$.

Accordingly, the Ring referred to in Formula (II) is formulae (i-a).

It will be appreciated that the six-membered ring may comprise a substituted pyridine ring or a substituted piperidine ring. Accordingly, in one embodiment, the compound may comprise a compound of formula (Ij):

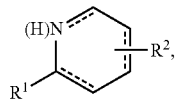

Formula Ij wherein $X^1$ is N or NH and one of $X^2$, $X^3$, $X^4$ or $X^5$ is $CR^2$ or $CHR^2$.

Accordingly, the Ring referred to in Formula (II) is formulae (ii).

In an alternative embodiment, the compound may comprise a compound of formula (Ik):

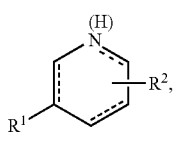

Formula Ik wherein $X^2$ is N or NH and one of $X^1$, $X^3$, $X^4$ or $X^5$ is $CR^2$ or $CHR^2$.

Accordingly, the Ring referred to in Formula (II) is formulae (ii).

In a further alternative embodiment, the compound may comprise a compound of formula (Il):

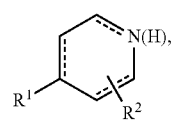

Formula Il wherein $X^3$ is N or NH and one of $X^1$, $X^2$, $X^4$ or $X^5$ is $CR^2$ or $CHR^2$.

Accordingly, the Ring referred to in Formula (II) is formulae (ii).

It will be appreciated that the six-membered ring may comprise a substituted diazine ring. Accordingly, in one embodiment the compound may comprise a compound of formula (Im):

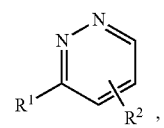

Formula Im wherein $X^1$ and $X^2$ are both N and one of $X^3$, $X^4$ or $X^5$ is $CR^2$.

Accordingly, the Ring referred to in Formula (II) is formulae (iii-b).

In an alternative embodiment, the compound may comprise a compound of formula (In):

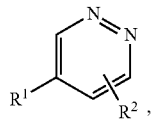

Formula In wherein $X^2$ and $X^3$ are both N and one of $X^1$, $X^4$ or $X^5$ is $CR^2$.

Accordingly, the Ring referred to in Formula (II) is formulae (iii-b).

In a further alternative embodiment, the compound may comprise a compound of formula (Io):

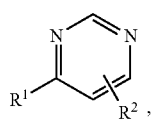

Formula Io wherein $X^1$ and $X^3$ are both N and one of $X^2$, $X^4$ or $X^5$ is $CR^2$.

Accordingly, the Ring referred to in Formula (II) is formulae (iv-b).

In a further alternative embodiment, the compound may comprise a compound of formula (Ip):

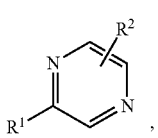

Formula Ip wherein $X^1$ and $X^4$ are both N and one of $X^2$, $X^3$ or $X^5$ is $CR^2$.

Accordingly, the Ring referred to in Formula (II) is formulae (v-b).

In a further alternative embodiment, the compound may comprise a compound of formula (Iq):

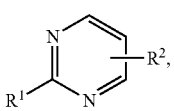

Formula Iq wherein $X^1$ and $X^5$ are both N and one of $X^2$, $X^3$ or $X^4$ is $CR^2$.

Accordingly, the Ring referred to in Formula (II) is formulae (v-b).

It will be appreciated that the six-membered ring may comprise a substituted piperazine ring. Accordingly, the compound may comprise a compound of formula (Ir):

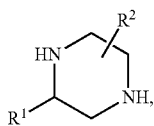

Formula Ir wherein $X^1$ and $X^4$ are both NH and one of $X^2$, $X^3$ or $X^5$ is $CHR^2$.

Accordingly, the Ring referred to in Formula (II) is formulae (v-a).

It will be appreciated that the six-membered ring may comprise a substituted triazine ring. Accordingly, the compound may comprise a compound of formula (Is):

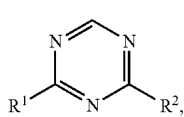

Formula Is wherein $X^1$, $X^3$ and $X^5$ are all N and $X^2$ is $CR^2$.

Accordingly, the Ring referred to in Formula (II) is formulae (vi-b).

$R^2$ may be an optionally substituted straight or branched alkyl or alkenyl group with 2 to 15 C atoms, 3 to 10 C atoms, or 4 to 7 C atoms.

In one embodiment, the backbone of the alkyl or alkenyl group is branched. Preferably, the branching consists of a $C_{1-4}$ alkyl group at any C position in the backbone. More preferably, the branching consists of a $C_{1-3}$ alkyl group at any C position in the backbone. Most preferably, the branching consists of a $C_{1-2}$ alkyl group at any C position in the backbone.

$R^2$ may be a straight chain or branched alkyl or alkylene with 6 to 15 C atoms, 8 to 12 C atoms or 8 to 10 C atoms, that is optionally mono- or polysubstituted by a $C_1$ to $C_4$ alkyl group. Preferably, $R^2$ comprises a $C_{4-5}$ alkyl group.

$R^2$ may be an optionally substituted alkyl or alkenyl group with a backbone comprising 2 to 15 C atoms, 3 to 10 C atoms, 4 to 7 C atoms or 4 to 5 C atoms. Preferably, $R^2$ comprises an optionally $C_{4-5}$ alkyl group.

$R^2$ may be substituted with a $C_{1-4}$ alkyl group. More preferably, $R^2$ is substituted with a $C_{1-3}$ alkyl group. Most preferably, $R^2$ is substituted with a $C_{1-2}$ alkyl group.

Accordingly, $R^2$ may be substituted with a methyl group or an ethyl group.

$R^2$ may be substituted at any C position in the chain.

In one embodiment $R^2$ may comprise a butyl group, a pentyl group, a 4-methylpentyl group, a 3-methylpentyl group, a 3-methylbutyl group, a 2-methylbutyl group or a 2-methylpentyl group. Preferably, $R^2$ comprises a butyl group, a pentyl group, a 3-methylpentyl group, a 3-methylbutyl group, a 2-methylbutyl group or a 2-methylpentyl group. Most preferably, $R^2$ comprises a 2-methylpentyl group.

$R^2$ may comprise one or more unsaturated bonds.

In one embodiment $R^2$ comprises one unsaturated bond. $R^2$ may comprise but-1-en-1-yl, butylidene, pent-1-en-1-yl or pentylidene. But-1-en-1-yl may comprise (1E)-but-1-en-1-yl or (1Z)-but-1-en-1-yl. Pent-1-en-1-yl may comprise (1E)-pent-1-en-1-yl or (1Z)-pent-1-en-1-yl.

In one embodiment, the backbone of the alkyl or alkenyl group is interrupted by one or more heteroatoms, preferably oxygen or nitrogen.

$R^2$ may comprise an (ethylamino)methyl group, a propoxymethyl group, an ethoxymethyl group or a propoxy group.

Where any group defined herein is an alkyl group, it may be a $C_1$, $C_2$, $C_3$ or $C_4$ alkyl, for example a methyl, ethyl, propyl or butyl group. Optionally, the alkyl group may be substituted with one or more heteroatoms, for example nitrogen, oxygen or a halogen.

Preferably, the compound is cis-2-(4-butylcyclohexyl) ethanoic acid, trans-2-(4-butylcyclohexyl)ethanoic acid, cis-2-(4-pentylcyclohexyl)ethanoic acid, trans-2-(4-pentylcyclohexyl)ethanoic acid, 2-(4-butylphenyl)ethanoic acid, 2-(4-pentylphenyl)ethanoic acid, cis-4-butylcyclohexanecarboxylic acid, trans-4-butylcyclohexanecarboxylic acid, cis-4-pentylcyclohexanecarboxylic acid, trans-4-pentylcyclohexanecarboxylic acid, 4-butylbenzoic acid, 4-pentylbenzoic acid, cis-[4-(4-methylpentyl)cyclohexyl]acetic acid, trans-[4-(4-methylpentyl)cyclohexyl]acetic acid, cis-[4-(3-methylpentyl)cyclohexyl]acetic acid, trans-[4-(3-methylpentyl)cyclohexyl]acetic acid, cis-4-(3-methylbutyl)cyclohexanecarboxylic acid, trans-4-(3-methylbutyl)cyclohexanecarboxylic acid, cis-4-(2-methylbutyl)cyclohexanecarboxylic acid, trans-4-(2-methylbutyl)cyclohexanecarboxylic acid, cis-[4-(2-methylpentyl)cyclohexyl]acetic acid, trans-[4-(2-methylpentyl)cyclohexyl]acetic acid, cis-4-[(1E)-but-1-en-1-yl]cyclohexanecarboxylic acid, trans-4-[(1E)-but-1-en-1-yl]cyclohexanecarboxylic acid, cis-(4-pentylidenecyclohexyl) acetic acid, trans-(4-pentylidenecyclohexyl)acetic acid, cis-4-(propoxymethyl)cyclohexyl acetic acid, trans-4-(propoxymethyl)cyclohexyl acetic acid, cis-5-butylpiperidine-2-carboxylic acid, trans-5-butylpiperidine-2-carboxylic acid, cis-{4-[(ethylamino)methyl] cyclohexyl}acetic acid, trans-{4-[(ethylamino)methyl] cyclohexyl}acetic acid, cis-4-(ethoxymethyl)cyclohexancarboxylic acid, trans-4-(ethoxymethyl)cyclohexancarboxylic acid, cis-4-propoxycyclohexanecarboxylic acid, trans-4-propoxycyclohexanecarboxylic acid, cis-2-(4-butylcyclohexyl)ethanamide, trans-2-(4-butylcyclohexyl)ethanamide, cis-2-(4-pentylcyclohexyl)ethanamide, trans-2-(4-pentylcyclohexyl)ethanamide, 2-(4-butylphenyl) ethanamide, 2-(4-pentylphenyl) ethanamide, cis-(4-butylcyclohexyl)formamide, trans-(4-butylcyclohexyl)formamide, cis-(4-pentylcyclohexyl)formamide, trans-(4-pentylcyclohexyl)formamide, 4-butylbenzamide, 4-pentylbenzamide, cis-[4-(4-methylpentyl)cyclohexyl]ethanamide, trans-[4-(4-methylpentyl)cyclohexyl]ethanamide, cis-[4-(3-methylpentyl)cyclohexyl]ethanamide, trans-[4-(3-methylpentyl)cyclohexyl]ethanamide, cis-4-(3-methylbutyl) cyclohexaneformamide, trans-4-(3-methylbutyl) cyclohexaneformamide, cis-4-(2-methylbutyl) cyclohexaneformamide, trans-4-(2-methylbutyl) cyclohexaneformamide, cis-[4-(2-methylpentyl)cyclohexyl] ethanamide, trans-[4-(2-methylpentyl)cyclohexyl] ethanamide, cis-4-[(1E)-but-1-en-1-yl] cyclohexaneformamide, trans-4-[(1E)-but-1-en-1-yl] cyclohexaneformamide, cis-(4-pentylidenecyclohexyl) ethanamide, trans-(4-pentylidenecyclohexyl)ethanamide, cis-4-(propoxymethyl)cyclohexylethanamide, trans-4-(propoxymethyl)cyclohexylethanamide, cis-5-butylpiperidine-2-formamide, trans-5-butylpiperidine-2-formamide, cis-{4-[(ethylamino)methyl]cyclohexyl}ethanamide, trans-{4-[(ethylamino)methyl]cyclohexyl}formamide, cis-4-(ethoxymethyl)cyclohexanformamide, trans-4-(ethoxymethyl)cyclohexanformamide, cis-4-propoxycyclohexaneformamide, trans-4- propoxycyclohexaneformamide, cis-4-butylcyclohexylmethylamine, trans-4-butylcyclohexylmethylamine, cis-4-pentylcyclohexylmethylamine, trans-4-pentylcyclohexylmethylamine, 4-butylbenzylamine, 4-pentylbenzylamine, cis-4-butylcyclohexylamine, trans-4-butylcyclohexylamine, cis-4-pentylcyclohexylamine, trans-4-pentylcyclohexylamine, 4-butylaniline, 4-pentylaniline, cis-[4-(4-methylpentyl)cyclohexyl]methylamine, trans-[4-(4-methylpentyl)cyclohexyl]methylamine, cis-[4-(3-methylpentyl)cyclohexyl]methylamine, trans-[4-(3-methylpentyl)cyclohexyl]methylamine, cis-4-(3-methylbutyl)cyclohexaneamine, trans-4-(3-methylbutyl)cyclohexaneamine, cis-4-(2-methylbutyl)cyclohexaneamine, trans-4-(2-methylbutyl)cyclohexaneamine, cis-[4-(2-methylpentyl)cyclohexyl]methylamine, trans-[4-(2-methylpentyl)cyclohexyl]methylamine, cis-4-[(1E)-but-1-en-1-yl]cyclohexaneamine, trans-4-[(1E)-but-1-en-1-yl]cyclohexaneamine, cis-(4-pentylidenecyclohexyl)methylamine, trans-(4-pentylidenecyclohexyl)methylamine, cis-4-(propoxymethyl)cyclohexylmethylamine, trans-4-(propoxymethyl)cyclohexylmethylamine, cis-5-butylpiperidine-2-amine, trans-5-butylpiperidine-2-amine, cis-{4-[(ethylamino)methyl]cyclohexyl}methylamine, trans-{4-[(ethylamino)methyl]cyclohexyl}amine, cis-4-(ethoxymethyl)cyclohexanamine, trans-4-(ethoxymethyl)cyclohexanamine, cis-4-propoxycyclohexaneamine, trans-4-propoxycyclohexaneamine.

Accordingly, in preferred embodiments, the present invention involves the use of a compound of formula (I), wherein:
$R^1$ is a carboxylic acid;
$X^1$ is CH or $CH_2$;
$X^2$ is CH or $CH_2$;
$X^3$ is $CHR^2$ or $CR^2$;
$X^4$ is CH or $CH_2$;
$X^5$ is CH or $CH_2$;
and $R^2$ is an optionally substituted straight or branched alkyl or alkenyl group with 1 to 20 C atoms, and wherein the backbone of the alkyl or alkenyl group is optionally interrupted by one or more heteroatoms; or a functional analogue, pharmaceutically acceptable salt or solvate thereof.

In more preferred embodiments, the present invention involves the use of a compound of formula (I), wherein:
$R^1$ is a carboxylic acid;
$X^1$ is CH or $CH_2$;
$X^2$ is CH or $CH_2$;
$X^3$ is $CHR^2$ or $CR^2$;
$X^4$ is CH or $CH_2$;
$X^5$ is CH or $CH_2$;
and $R^2$ is straight alkyl group with 1 to 20 C atoms, and wherein the backbone of the alkyl group is optionally interrupted by one or more heteroatoms; or a functional analogue, pharmaceutically acceptable salt or solvate thereof.

In more preferred embodiments, the present invention involves the use of a compound of formula (I), wherein:
$R^1$ is a carboxylic acid;
$X^1$ is CH or $CH_2$;
$X^2$ is CH or $CH_2$;
$X^3$ is $CHR^2$ or $CR^2$;
$X^4$ is CH or $CH_2$;
$X^5$ is CH or $CH_2$;
and $R^2$ is straight alkyl group with 2 to 7 C atoms, and wherein the backbone of the alkyl group is optionally interrupted by one or more heteroatoms; or a functional analogue, pharmaceutically acceptable salt or solvate thereof.

In more preferred embodiments, the present invention involves the use of a compound of formula (I), wherein:
$R^1$ is a carboxylic acid;
$X^1$ is CH or $CH_2$;
$X^2$ is CH or $CH_2$;
$X^3$ is $CHR^2$ or $CR^2$;
$X^4$ is CH or $CH_2$;
$X^5$ is CH or $CH_2$;
and $R^2$ is an optionally substituted alkyl or alkenyl group with a backbone comprising 3 to 10 C atoms, and wherein the backbone of the alkyl group is optionally interrupted by one or more heteroatoms; or a functional analogue, pharmaceutically acceptable salt or solvate thereof.

In a most preferred embodiment, the compound is 2-(4-pentylcyclohexyl)ethanoic acid, and preferably trans-2-(4-pentylcyclohexyl)ethanoic acid.

In another most preferred embodiment, the compound is 2-(4-pentylphenyl)ethanoic acid.

In another most preferred embodiment, the compound is 4-butylcyclohexanecarboxylic acid.

In another most preferred embodiment, the compound is 4-butylbenzoic acid.

In another most preferred embodiment, the compound is [4-(4-methylpentyl)cyclohexyl]acetic acid.

In another most preferred embodiment, the compound is [4-(3-methylpentyl)cyclohexyl]acetic acid.

In another most preferred embodiment, the compound is 4-(3-methylbutyl)cyclohexanecarboxylic acid.

In another most preferred embodiment, the compound is 4-(2-methylbutyl)cyclohexanecarboxylic acid.

In another most preferred embodiment, the compound is [4-(2-methylpentyl)cyclohexyl]acetic acid.

In another most preferred embodiment, the compound is 4-[(1E)-but-1-en-1-yl]cyclohexanecarboxylic acid.

In another most preferred embodiment, the compound is (4-pentylidenecyclohexyl) acetic acid.

In another most preferred embodiment, the compound is 4-(propoxymethyl)cyclohexyl acetic acid.

In another most preferred embodiment, the compound is 5-butylpiperidine-2-carboxylic acid.

In another most preferred embodiment, the compound is {4-[(ethylamino)methyl]cyclohexyl}acetic acid.

In another most preferred embodiment, the compound is 4-(ethoxymethyl)cyclohexancarboxylic acid.

In another most preferred embodiment, the compound is 4-propoxycyclohexanecarboxylic acid.

The compound may be as defined above with the proviso that the compound is not hexylbenzoic acid.

The compound may be as defined above with the proviso that the compound is not pentylbenzoic acid.

Two of the compounds listed above, which have shown very promising results, are [4-(2-methylpentyl)cyclohexyl] acetic acid and 4-(2-methylbutyl)cyclohexylcarboxylic acid. Both of these compounds comprise an $R^2$ group which is an alkyl, substituted with a methyl group in the two position. Accordingly, it will be appreciated that these compounds spatially are very similar to bicyclic compounds comprising two fused six-membered rings.

Accordingly, in some embodiments the Ring referred to in Formula (II) is selected from one of formulae (vii) to (xi).

The Ring referred to in Formula (II) may be selected from one of formulae (vii-a) to (xi-a):

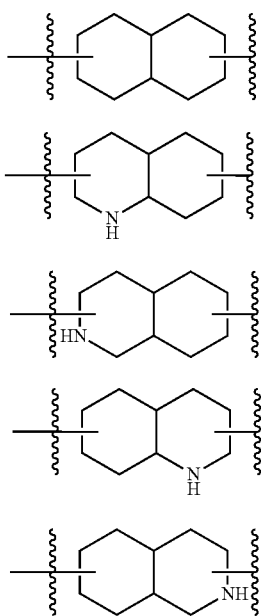

(vii-a)

(viii-a)

(ix-a)

(x-a)

(xi-a)

Alternatively, the Ring referred to in Formula (II) may be selected from one of formulae (vii-b) to (xi-b):

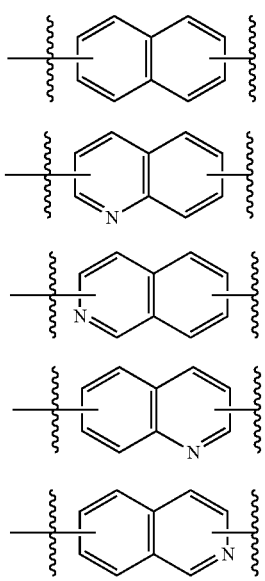

(vii-a)

(viii-a)

(ix-a)

(x-a)

(xi-a)

Preferably, Ring comprises formula (vii).

Accordingly, the compound may comprise a compound of formula (III):

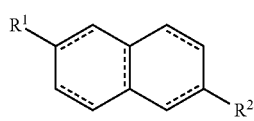

Formula (III)

$R^2$ may be an optionally substituted alkyl or alkenyl group with a backbone comprising 1 to 15 C atoms, 1 to 10 C atoms, 1 to 7 C atoms, 1 to 5 C atoms or 2 to 4 C atoms.

$R^2$ may be substituted with a $C_{1-4}$ alkyl group. More preferably, the branching consists of a $C_{1-3}$ alkyl group. Most preferably, $R^2$ is substituted with a $C_{1-2}$ alkyl group.

Accordingly, $R^2$ may be substituted with a methyl group or an ethyl group.

$R^2$ may be substituted at any C position in the chain.

In one embodiment $R^2$ may comprise a methyl group, an ethyl group, a propyl group or a butyl group. Preferably $R^2$ comprises a propyl group.

$R^2$ may comprise one or more unsaturated bonds.

In one embodiment, the backbone of the alkyl or alkenyl group is interrupted by one or more heteroatoms, preferably oxygen or nitrogen.

Accordingly, the compound may comprise a compound of formula (IIIa):

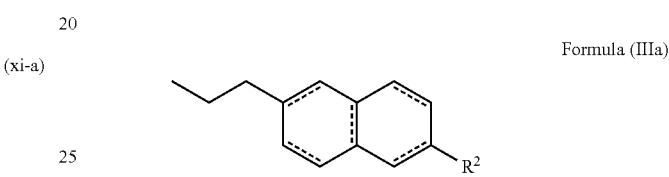

Formula (IIIa)

$R^1$ may be selected from a carboxylic acid, amide or amine group with 1 to 5 C atoms, preferably with 1 to 3 C atoms, more preferably with 1 to 2 C atoms. Preferably, $R^1$ is a carboxylic acid with 1 to 5 C atoms, preferably 1 to 3 C atoms, more preferably 1 to 2 C atoms. Preferably, $R^1$ comprises methanoic acid or ethanoic acid.

Accordingly, the compound may comprise a compound of formula (IIIb):

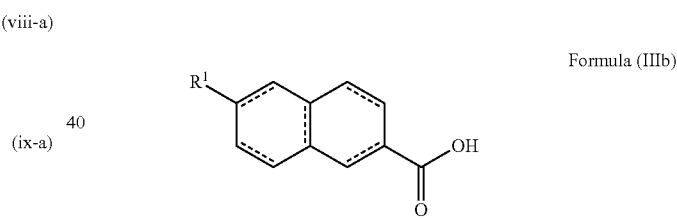

Formula (IIIb)

Alternatively, the compound may comprise a compound of formula (IIIc):

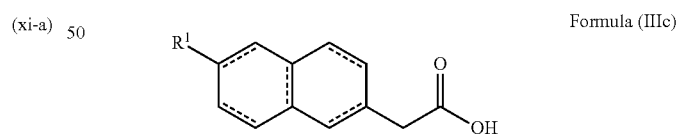

Formula (IIIc)

The compound may comprise a compound of formula (IIId):

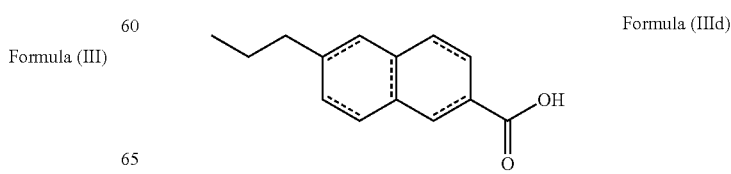

Formula (IIId)

Alternatively, the compound may comprise a compound of formula (IIIe):

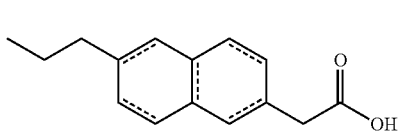

Formula (IIIe)

Preferably, the compound is (6-propylnapthalen-2-yl)acetic acid, 6-propylnaphthalene-2-carboxylic acid, 6-propyldecahydronaphthalene-2-carboxylic acid, 6-propyldecahydronaphthalene-2-acetic acid, (6-propylnapthalen-2-yl)ethanamide, 6-propylnaphthalene-2-formamide, 6-propyldecahydronaphthalene-2-formamide, 6-propyldecahydronaphthalene-2-ethanamide, (6-propylnapthalen-2-yl)methyl amine, 6-propylnaphthalene-2-amine, 6-propyldecahydronaphthalene-2-amine or 6-propyldecahydronaphthalene-2-methyl amine.

In a most preferred embodiment, the compound is (6-propylnapthalen-2-yl)acetic acid.

In another most preferred embodiment, the compound is 6-propylnaphthalene-2-carboxylic acid.

In another most preferred embodiment, the compound is 6-propyldecahydronaphthalene-2-carboxylic acid.

In another most preferred embodiment, the compound is 6-propyldecahydronaphthalene-2-acetic acid.

It is believed that a number of the compounds that have been synthesised are novel per se.

In accordance with a fourth aspect, therefore, there is provided a compound selected from [4-(4-methylpentyl)cyclohexyl]acetic acid; [4-(3-methylpentyl)cyclohexyl]acetic acid; 4-(3-methylbutyl)cyclohexanecarboxylic acid; 4-(2-methylbutyl)cyclohexanecarboxylic acid; [4-(2-methylpentyl)cyclohexyl]acetic acid; 4-[(1E)-but-1-en-1-yl]cyclohexanecarboxylic acid; (4-pentylidenecyclohexyl)acetic acid; 4-(propoxymethyl)cyclohexyl acetic acid; 5-butylpiperidine-2-carboxylic acid; {4-[(ethylamino)methyl]cyclohexyl}acetic acid; 4-(ethoxymethyl)cyclohexancarboxylic acid; and 4-propoxycyclohexanecarboxylic acid.

In a fifth aspect, there is provided a compound of formula (I):

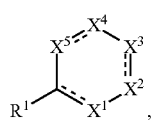

Formula (I)

wherein:
$R^1$ is a carboxylic acid, amide or amine;
$X^1$ is $CHR^2$, $CR^2$, CH, $CH_2$, N or NH;
$X^2$ is $CHR^2$, $CR^2$, CH, $CH_2$, N or NH;
$X^3$ is $CHR^2$, $CR^2$, CH, $CH_2$, N or NH;
$X^4$ is $CHR^2$, $CR^2$, CH, $CH_2$, N or NH;
$X^5$ is $CHR^2$, $CR^2$, CH, $CH_2$, N or NH; and
wherein one of $X^1$, $X^2$, $X^3$, $X^4$ and $X^5$ is $CHR^2$ or $CR^2$; and $R^2$ is an optionally substituted straight or branched alkyl or alkenyl group with 1 to 20 C atoms, and wherein the backbone of the alkyl or alkenyl group is optionally interrupted by one or more heteroatoms; or a functional analogue, pharmaceutically acceptable salt or solvate thereof, for use in therapy or as a medicament.

Accordingly, in a sixth aspect, there is provided a compound of formula (I):

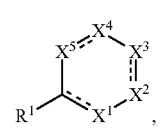

Formula (I)

wherein:
$R^1$ is a carboxylic acid, amide or amine;
$X^1$ is $CHR^2$, $CR^2$, CH, $CH_2$, N or NH;
$X^2$ is $CHR^2$, $CR^2$, CH, $CH_2$, N or NH;
$X^3$ is $CHR^2$, $CR^2$, CH, $CH_2$, N or NH;
$X^4$ is $CHR^2$, $CR^2$, CH, $CH_2$, N or NH;
$X^5$ is $CHR^2$, $CR^2$, CH, $CH_2$, N or NH; and
wherein one of $X^1$, $X^2$, $X^3$, $X^4$ and $X^5$ is $CHR^2$ or $CR^2$; and $R^2$ is an optionally substituted straight or branched alkyl or alkenyl group with 1 to 20 C atoms, and wherein the backbone of the alkyl or alkenyl group is optionally interrupted by one or more heteroatoms; for use in treating, preventing or ameliorating a seizure-related disorder, bipolar disorder, mania, migraine, Alzheimer's disease, Parkinson's disease or stroke.

It will be appreciated that the compound according to the first or fifth aspect, or a functional analogue, pharmaceutically acceptable salt or solvate thereof may be used in a medicament which may be used in a monotherapy (i.e. use of the compound alone), for treating, ameliorating, or preventing seizure-related disorders, bipolar disorders, mania, migraine, Alzheimer's disease, Parkinson's disease or stroke. Alternatively, the compound of first or fifth aspect, or a functional analogue, pharmaceutically acceptable salt or solvate thereof may be used as an adjunct to, or in combination with, known therapies for treating, ameliorating, or preventing seizure-related disorders, bipolar disorders, mania, migraine, Alzheimer's disease, Parkinson's disease or stroke.

The compound of the first or fifth aspect, or a functional analogue, pharmaceutically acceptable salt or solvate thereof may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given.

Medicaments comprising the compound of the first or fifth aspect, or a functional analogue, pharmaceutically acceptable salt or solvate thereof may be used in a number of ways. For instance, oral administration may be required, in which case the compound may be contained within a composition that may, for example, be ingested orally in the form of a tablet, capsule or liquid. Compositions comprising the compounds of the invention may be administered by inhalation (e.g. intranasally). Compositions may also be formulated for topical use. For instance, creams or ointments may be applied to the skin.

Compounds according to the invention may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with compounds used according to the invention is required and which would normally require frequent administration (e.g. at least daily injection).

In a preferred embodiment, compounds and compositions according to the invention may be administered to a subject by injection into the blood stream or directly into a site requiring treatment. Injections may be intravenous (bolus or infusion) or subcutaneous (bolus or infusion), or intradermal (bolus or infusion).

It will be appreciated that the amount of the compound that is required is determined by its biological activity and bioavailability, which in turn depends on the mode of administration, the physiochemical properties of the compound, and whether it is being used as a monotherapy, or in a combined therapy. The frequency of administration will also be influenced by the half-life of the compound within the subject being treated. Optimal dosages to be administered may be determined by those skilled in the art, and will vary with the particular compound in use, the strength of the pharmaceutical composition, the mode of administration, and the advancement of the cancer. Additional factors depending on the particular subject being treated will result in a need to adjust dosages, including subject age, weight, gender, diet, and time of administration.

Generally, a daily dose of between 0.01 µg/kg of body weight and 500 mg/kg of body weight of the compound according to the invention may be used for treating, ameliorating, or preventing seizure-related disorders, bipolar disorders, mania, migraine, Alzheimer's disease, Parkinson's disease or stroke depending upon which compound or analogue is used. More preferably, the daily dose is between 0.01 mg/kg of body weight and 400 mg/kg of body weight, more preferably between 0.1 mg/kg and 200 mg/kg body weight, and most preferably between approximately 1 mg/kg and 100 mg/kg body weight.

The compound may be administered before, during or after onset of the seizure-related disorder, bipolar disorder, mania, migraine, Alzheimer's disease, Parkinson's disease or stroke to be treated. Daily doses may be given as a single administration (e.g. a single daily injection). Alternatively, the seizure-related disorder, bipolar disorder, mania, migraine, Alzheimer's disease, Parkinson's disease or stroke may require administration twice or more times during a day. As an example, a compound according to the first or fifth aspect may be administered as two (or more depending upon the severity of the seizure-related disorder, bipolar disorder, mania, migraine, Alzheimer's disease, Parkinson's disease or stroke being treated) daily doses of between 25 mg and 7000 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of the compounds according to the invention to a patient without the need to administer repeated doses.

Known procedures, such as those conventionally employed by the pharmaceutical industry (e.g. in vivo experimentation, clinical trials, etc.), may be used to form specific formulations comprising the compounds according to the invention and precise therapeutic regimes (such as daily doses of the compounds and the frequency of administration). The inventors believe that they are the first to describe a pharmaceutical composition for treating seizure-related disorder, bipolar disorder, mania, migraine, Alzheimer's disease, Parkinson's disease or stroke, based on the use of the compounds of the invention.

Hence, in a seventh aspect of the invention, there is provided a pharmaceutical composition comprising a compound according to the first or fifth aspect, or a functional analogue, pharmaceutically acceptable salt or solvate thereof, and a pharmaceutically acceptable vehicle.

The pharmaceutical composition can be used in the therapeutic amelioration, prevention or treatment in a subject of seizure-related disorders, bipolar disorders, mania, migraine, Alzheimer's disease, Parkinson's disease or stroke, and preferably epilepsy. Thus, the composition is preferably an anticonvulsant pharmaceutical composition.

Preferably, the composition comprises a compound of the first or fifth aspects.

The invention also provides, in an eighth aspect, a process for making the composition according to the seventh aspect, the process comprising contacting a therapeutically effective amount of a compound of the first or fifth aspect, or a functional analogue, pharmaceutically acceptable salt or solvate thereof, and a pharmaceutically acceptable vehicle.

A "subject" may be a vertebrate, mammal, or domestic animal. Hence, compounds, compositions and medicaments according to the invention may be used to treat any mammal, for example livestock (e.g. a horse), pets, or may be used in other veterinary applications. Most preferably, however, the subject is a human being.

A "therapeutically effective amount" of compound is any amount which, when administered to a subject, is the amount of drug that is needed to treat the target disease, or produce the desired effect, i.e. inhibits seizures.

For example, the therapeutically effective amount of compound used may be from about 0.01 mg to about 800 mg, and preferably from about 0.01 mg to about 500 mg. It is preferred that the amount of compound is an amount from about 0.1 mg to about 250 mg, and most preferably from about 0.1 mg to about 20 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents (i.e. the compound according to the first or fifth aspects) according to the invention. In tablets, the active compound may be mixed with a vehicle having the necessary compression properties in suitable proportions and compacted in the shape and size desired. The powders and tablets preferably contain up to 99% of the active compound. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution.

Liquid vehicles are used in preparing solutions, suspensions, emulsions, syrups, elixirs and pressurized compositions.

The compound according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The compound may be prepared as a sterile solid composition that may be dissolved or suspended at the time of administration using sterile water, saline, or other appropriate sterile injectable medium.

The compound and compositions of the invention may be administered in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The compounds used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

All features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

Figure 6:
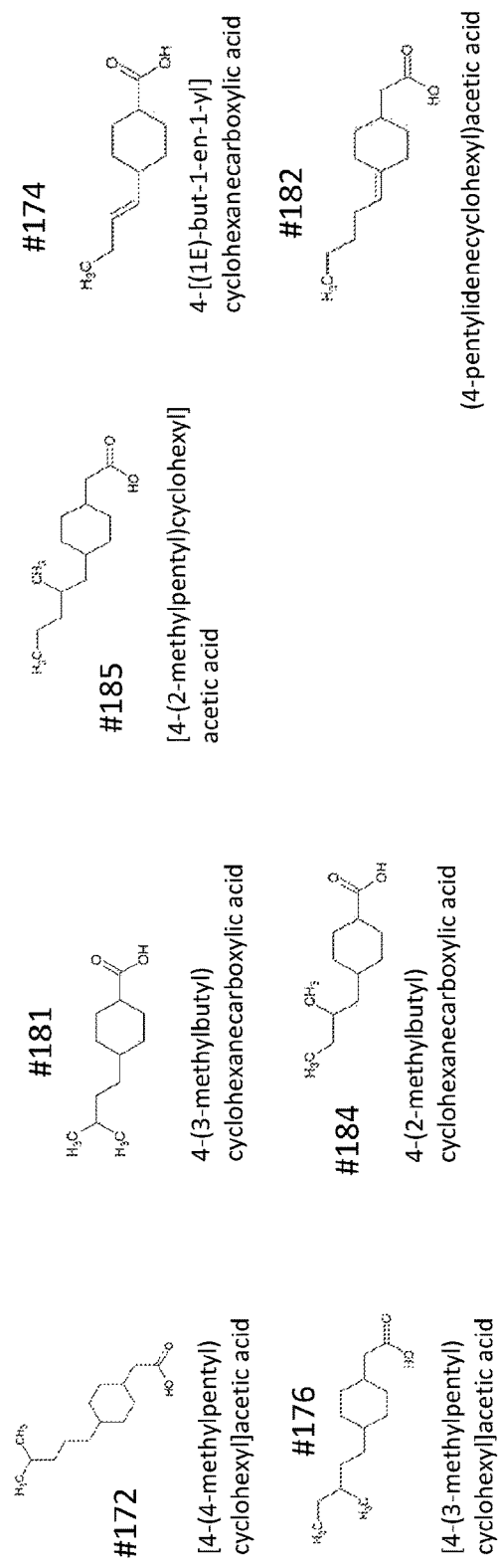
Figure 7:
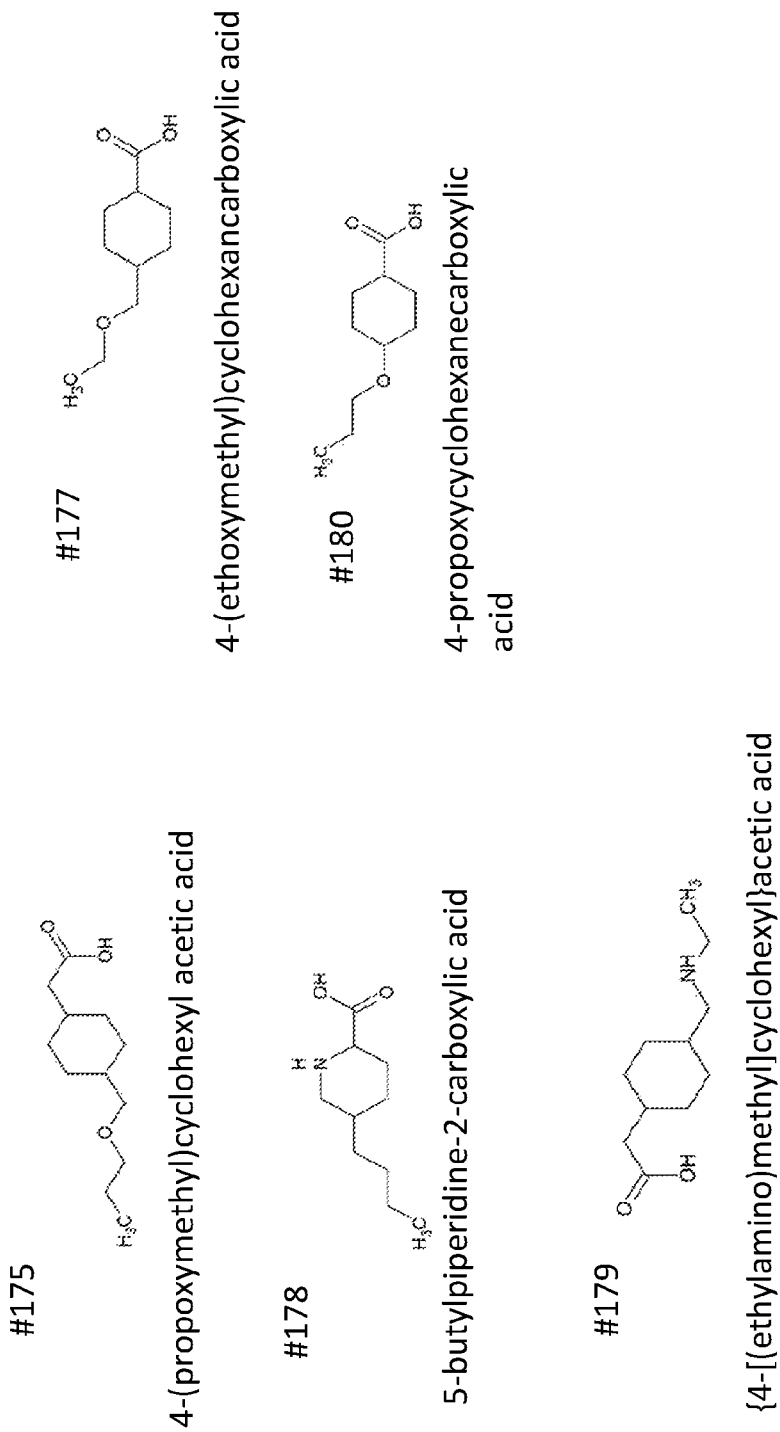
Figure 8:
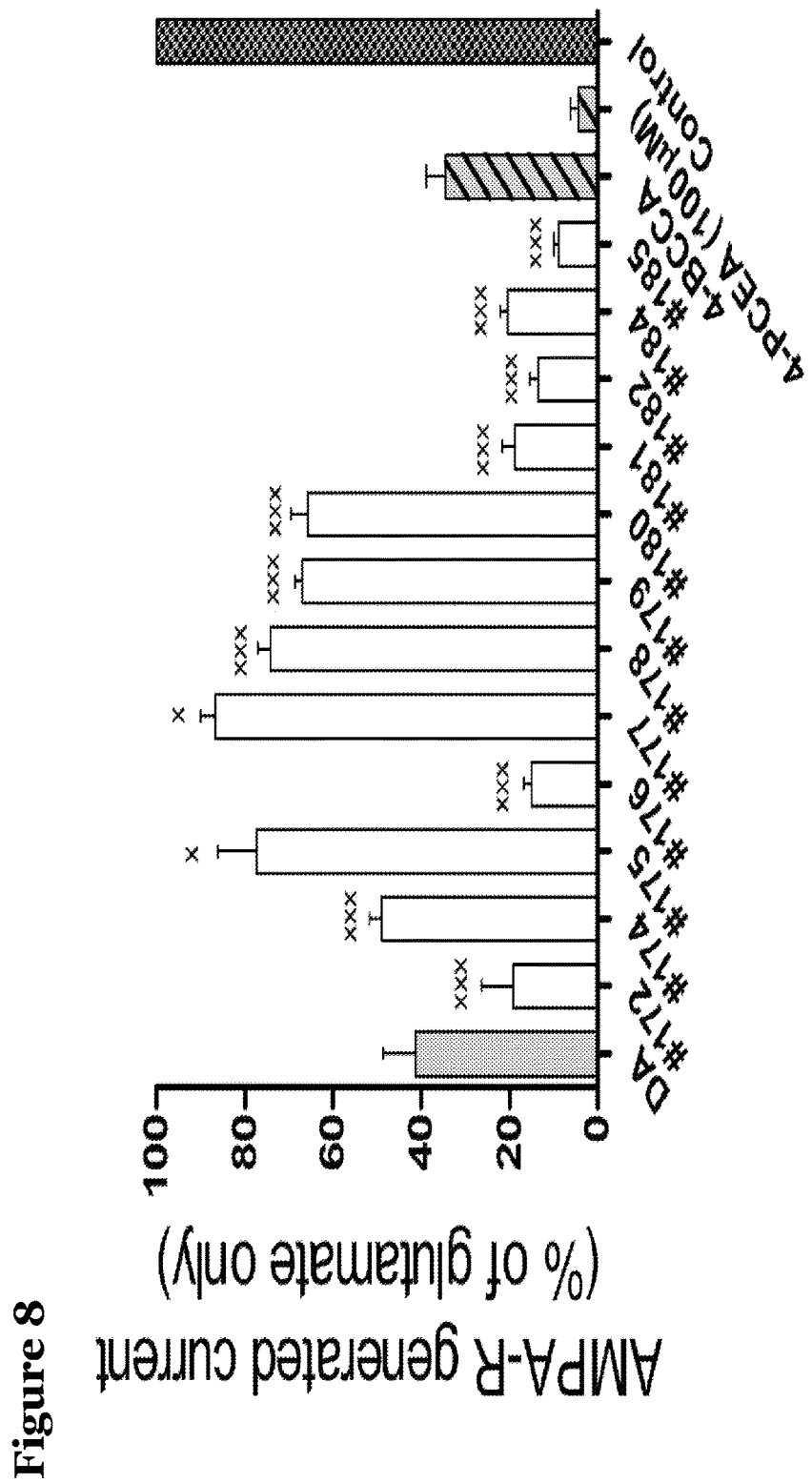
Figure 9:
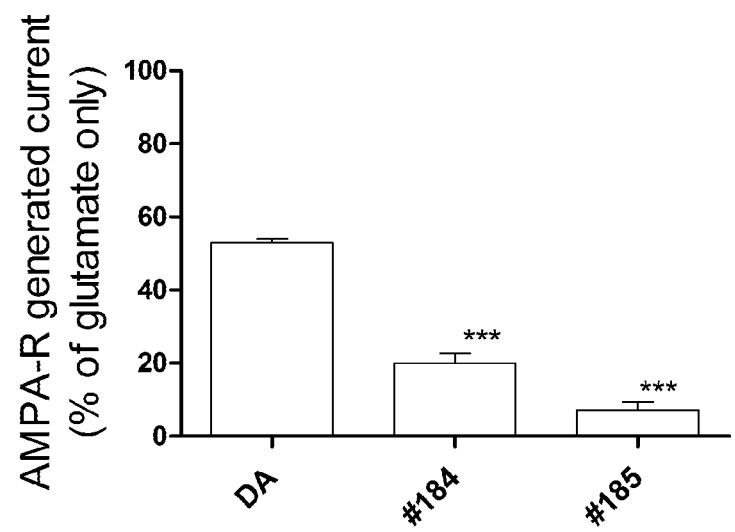

FIG. 5 is a table showing in vivo seizure control data for 4-BCCA in comparison to a widely used seizure control treatment, valproic acid (VPA), showing single dose data protection against multiple seizure models for 4-BCCA and a potency estimation (ED50) for each model for 4-BCCA and VPA;

FIG. 6 shows the structures of compounds containing branched chains or a double bond in the chain;

FIG. 7 shows the structures of compounds containing heteroatoms in the chain or in the six-membered ring;

FIG. 8 shows the inhibitory activity for decanoic acid (DA), 4-BCCA, 4-PCEA and the compounds shown in FIGS. 6 and 7 for AMPA receptor GluA2/3; and FIG. 9 shows the inhibitory activity for decanoic acid (DA) and some of the compounds shown in FIGS. 6 and 7 for AMPA receptor GluA1/2.

EXAMPLE 1

The inventors investigated the use of a new family of cyclic compounds in seizure control. In these experiments the inventors used AMPA receptors expressed in *xenopus* oocytes to measure inhibition of receptor activity by cyclic compounds using an electrophysiology approach. The inventors also used rat entorhinal cortex-hippocampus slices exposed to the GABA(A) receptor antagonist pentelenetetrazol (PTZ) which is widely used to generate seizures and seizure-like (paroxysmal) activity, to assess seizure control activity (Armand et al., 1998). The inventors also measured histone deacetylase (HDAC) inhibition; this can cause teratogenic effects (Jentink et al., 2010) and has been proposed to explain the teratogenicity of the branched isomer of octanoic acid, valproic acid (2-propylpentanoic acid), a well-established epilepsy treatment (Eikel et al., 2006; Phiel et al., 2001). Finally, the inventors analyzed in vivo efficacy of one of the compounds within the family using distinct in vivo models. Accordingly, the inventors have identified novel compounds providing strongly enhanced seizure control activity compared to valproic acid, suggesting a potential new treatment for drug resistant epilepsy. Given the mechanistic similarities between seizure-related disorders, bipolar disorders, mania, migraine, Alzheimer's disease, Parkinson's disease and stroke, the inventors believe that any of these conditions can be effectively treated with the novel compounds described herein.

Experimental Procedures

Animals

Adult male CF No 1 albino mice (18-25 g MES and 26-30 g 6 Hz) and male Sprague-Dawley albino rats (100-150 g)

were obtained from Charles River, Portage, Mich., and were matched, where possible, for sex, age, and weight (Petty and Karler, 1965; Woolley et al., 1961). Animals were maintained on an adequate diet (Prolab RMH 3000), allowed free access to food and water (Davenport and Davenport, 1948) and allowed time to correct where necessary after transit. All mice were housed in a dedicated facility, in plastic cages with controlled humidity, exchange of air and controlled lighting (12 h light/dark cycle). The animals were housed, fed, and handled in a manner consistent with the recommendations in the National Council Publication, "Guide for the Care and Use of Laboratory animals". No insecticides capable of altering hepatic drug metabolism enzymes are used in the animal facility.

Compounds for Analysis

Fatty acids used in this study were: valproic acid (VPA) (Sigma), octanoic acid (OA) (Alfa Aesar), nonanoic acid (NA), decanoic acid (DA), 4-ethyloctanoic acid (4-EOA) (Chemos GmbH), trans-4-butylcyclohexane carboxylic acid (4-BCCA) (TCI), 4-butylbenzoic acid (4-BBA), a racemic mixture of both trans- and cis-2-(4-pentylcyclohexyl)ethanoic acid (4-PCEA) and 4-pentylphenylethanoic acid (4-PPEA). Compounds were prepared as 1000 times stocks (1 M) in dimethyl sulfoxide (DMSO), except for VPA which was dissolved in distilled water. Stocks were dissolved in artificial cerebrospinal fluid (aCSF) or media to achieve their final experimental concentrations of 1 mM.

In Vitro RNA Transcription of AMPA Receptor Subunits

The AMPA receptor (flip isoform) cDNAs inserted in a SP6 polymerase expression vector (pSP6T) were a generous gift from Prof Ralf Schoepfer (NPP, UCL). RNA was transcribed in vitro from Mlu I linearized transcripts using the SP6 Promega RiboMax RNA synthesis kit (Madison, Wis.) according to manufacturer's protocols except for the addition of 0.75 mM capping nucleotide m7G(5')ppp(5')G (Promega, Madison, Wis.) and 1.6 mM GTP. cRNA concentrations and integrity were estimated by the intensity of fluorescence bands in RNA denaturating gels. AMPA receptor cRNAs were mixed in a nominal 1:1 ratio and approximately 5 ng was injected per oocyte.

Oocyte Preparation and Injection

*Xenopus laevis* oocytes were purchased from the European *Xenopus* Resource Centre, University of Portsmouth. Stage V to VI oocytes were mechanically dissected and then subjected to gentle shaking for approximately 30-50 min at room temperature with modified Barth's solution (in mM): NaCl 88, KCl 1, NaHCO$_3$ 2.4, MgCl$_2$ 0.82, CaCl$_2$ 0.77, Tris-Cl 15, adjusted to pH 7.4 with NaOH (Sigma-Aldrich, UK), supplemented with 50 IU/ml penicillin and 50 µg/ml streptomycin (Invitrogen, UK) and 50 µg/ml tetracycline (Sigma-Aldrich, UK) and 1% collagenase (type 1A). Healthy oocytes were manually defolliculated and the injections of cRNA for homomeric subunits alone (GluA1), or heteromeric mixtures of two subunits together (GluA2/GluA3) were made using an automated Drummond Nanoinject II injector (Broomall, Pa.). The oocytes were then incubated at 17° C. in modified Barth's solution for at least 48 hours before use in electrophysiological recordings.

Electrophysiological Recordings from Oocytes

Experiments were performed at room temperature (approximately 21-23° C.). An oocyte was placed in a recording chamber (0.3-0.5 ml volume) and perfused with ND96 solution (96 mM NaCl, 2 mM KCl, 1.8 mM CaCl$_2$, 1 mM MgCl$_2$, 5 mM HEPES, with pH adjusted to 7.5). Current and voltage electrodes were filled with 300 mM KCl and made from thin-walled borosilicate glass (GC150TF-7.5, Harvard Apparatus, Kent, UK) using a PC-10 electrode puller (Narashige Instruments, Japan) and had resistances of 0.5-2 MΩ. Oocytes were voltage-clamped to a holding potential of −50 mV or −60 mV using a Turbo TEC-03 amplifier (npi electronics, Tamm, Germany). Compounds were dissolved in distilled water or DMSO and dissolved in bathing solution to achieve their final concentrations during experiments, and were applied under gravity flow during the experiment by using a multi-valve perfusion system (VC3-8C, ALA Scientific Instruments, Farmingdale, N.Y.). The bath solutions were perfused at a rate of 10 ml/min. Recordings were filtered at 20 Hz and digitized at 100 Hz (Digidata 1322A, Molecular Devices, Sunnyvale, Calif.) before recording to computer hard disk. Data acquisition was performed using the Windows PC based programme, WinEDR v3.0.6 (John Dempster, University of Strathclyde, UK).

Data Analysis

The data from the electrophysiology experiments were analyzed using GraphPad Prism software (GraphPad software, San Diego Calif., USA) and SPSS (IBM United Kingdom Limited). Statistical analysis was performed using ANOVA with Dunnett's or Tukey post hoc test, pair t-test or un-pair t-test. For the behavior experiment, the nonparametric test, Mann-Whitney test were used. Differences were considered as significant at $P<0.05$.

In Vitro Electrophysiology

The preparation of entorhinal cortex-hippocampus slices and electrophysiological recording in CA1 were described previously (Armand et al., 1998; Chang and Walker, 2011). In brief, male rats (50-150 g) were decapitated after killing by intraperitoneal injection with an overdose of pentobarbitone (500 mg/kg). The brain was removed and preserved in oxygenated ice-cold sucrose solution in mM: NaCl 87, KCl 2.5, MgCl$_2$ 7, CaCl$_2$ 0.5, NaH$_2$PO$_4$ 1.25, NaHCO$_3$ 26.2 sucrose 75, glucose 3. Transverse slices (350 µm) were prepared with a vibratome (VIBRATOME® 1500, Intracel Ltd) and were then stored in an interface chamber containing artificial cerebrospinal fluid solution (aCSF) in mM: NaCl 119, KCl 2.5, MgSO$_4$ 1.3, CaCl$_2$ 2.5, NaH$_2$PO$_4$ 1, NaHCO$_3$ 26.2 glucose 16.6. The slices were stored for over one hour. During the experiment, the slices were transferred from the interface chamber into a submerged recording chamber and continuously perfused with prewarmed (about 36° C.) oxygenated (95% O$_2$, 5% CO$_2$) aCSF. A field potential recording was made by placing a glass microelectrodes filled with aCSF solution in stratum *radiatum* of CA1. A bipolar stimulating electrode was positioned in the Schaffer collateral/commissural fiber pathway in stratum *radiatum* to confirm slice viability. Pentelenetetrazol (PTZ) (2 mM) was added to the perfusate and [K$^+$] was increased to 6 mM in order to induce epileptiform activity. Compounds were applied once the frequency and amplitude of the epileptiform discharges were stable over a period of 10 min. Anticonvulsant effects were evaluated by measuring the frequency of the discharges every minute.

HDAC Activity Assay

Histone deacetylase activity was analyzed by using an in vitro commercial assay kit, the HDAC fluorescent activity assay/drug discovery kit HDAC activity (Biomol, Plymouth Meeting, Pa.). The assay was conducted at room temperature according to the manufacturer's protocol, using Trichostatin A (a HDAC inhibitor; at 1 µM concentration) as a positive control. Data were derived from at least triplicate experiments with each experiment comprising at least duplicate measurements (n=6) normalized to controls (without VPA or fatty acids).

In Vivo Seizure Models
The 6 Hz "Psychomotor" Seizure Test

Adult male CF1 mice (18-25 g) were pretreated intraperitoneally (i.p.) with each compound at 100-150 mg/kg. After pretreatment, each mouse was given a drop of 0.5% tetracaine hydrochloride to each eye, following by low-frequency (6 Hz) stimulation (32 mA) for 3 seconds delivered through corneal electrodes. Animals were manually restrained and released immediately following the stimulation and observed for the presence or absence of seizure activity at five time points (1/4, 1/2, 1, 2, and 4 hours). Typically, the 6 Hz stimulation results in a seizure characterized by a minimal clonic phase that is followed by stereotyped, automatic behaviors, including twitching of the vibrissae, and Straub-tail. Animals not displaying such behaviors were considered protected.

Maximal Electroshock Test (MES)

The MES is a model for generalized tonic-clonic seizures which provides an indication of a compound's ability to prevent seizure spread when all neuronal circuits in the brain are maximally active. Animals are pretreated with compounds (100-125 mg/kg) by i.p. injection. Seizure activity was induced by delivery of 60 Hz of alternating current (50 mA in mice, 150 in rats) for 0.2 s through corneal electrodes which had been primed with an electrolyte solution containing an anesthetic agent (0.5% tetracaine HCl). An animal is considered "protected" from MES-induced seizures upon abolition of the hind limb tonic extensor component of the seizure (Swinyard et al., 1995; White et al., 1995; White et al., 2007).

Subcutaneous Metrazol Seizure Threshold Test (scMET)

Subcutaneous injection of Metrazol produces clonic seizures in animals. The scMET test allowed detection of test compound efficacy in raising seizure threshold, thus demonstrating protection from clonic seizure induction. Animals were pretreated with each compound (100 mg/kg) in a similar manner to the MES test. Seizure activity was induced by administration of Metrazol (CD97: 85 mg/kg mice; 70 mg/kg rats) into skin in the midline of the neck. Animals were observed for the following 30 minutes for the presence or absence of a seizure. Animals were considered "protected" if they did not exhibit an episode of clonic spasms of the fore and/or hindlimbs, jaws, or vibrissae (3-5 seconds).

Corneal Kindled Mouse Model (CKM)

This model involves the use of corneal kindled mouse model for prediction of efficacy in human partial seizures (Rowley and White, 2010). Adult male CF1 mice (18-25 g) mice were stimulated through corneal electrodes (3 mA, 60 Hz, 3 seconds) after administration of 0.5% tetracaine hydrochloride to each eye. This procedure was carried out twice daily for an average of 12 days. Animals were considered kindled when they displayed five consecutive stage five seizures according to the Racine scale (Racine, 1972):
  Stage 1, facial automatisms;
  Stage 2: head nodding and more serve facial and mouth movements (jaw-opening);
  Stage 3: rats display forelimb clonus with a lordotic posture;
  Stage 4: bilateral forelimb clonus continues along with rearing; and
  Stage 5: some rats will fall to one side first and then show evidence of forelimb clonus.

After 5-7-days stimulation-free period once the mice were fully kindled, the test compounds were administrated (100 mg/kg, i.p.). Mice in each group were then tested at various time points (0.25, 0.5, 1, 2, 4 hours) after drug dosing. Mice displaying a seizure score <3 are considered protected.

Statistical Analyses

In all data provided results are presented as mean±the standard error of the mean (SEM). Statistical comparisons were performed by using the one way ANOVA followed by Tukey for post hoc analysis using GraphPad.

Results

Compounds

Figure 1:
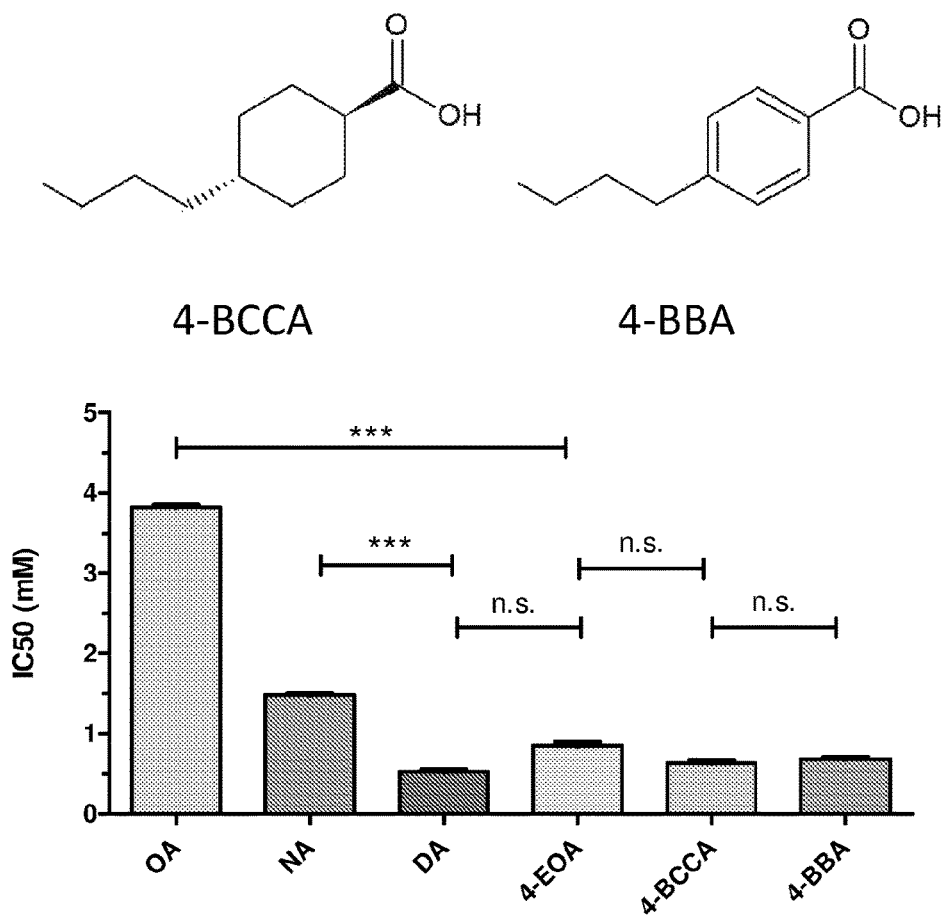
FIG. 1 shows the structures of trans-4-butylcyclohexane carboxylic acid (4-BCCA) and 4-butylbenzoic acid (4-BBA), and a graph showing the potency (IC50) of 4-BCCA and 4-BBA compared to straight chain and branched derivatives of fatty acids for AMPA receptor mediated current.
Figure 2:
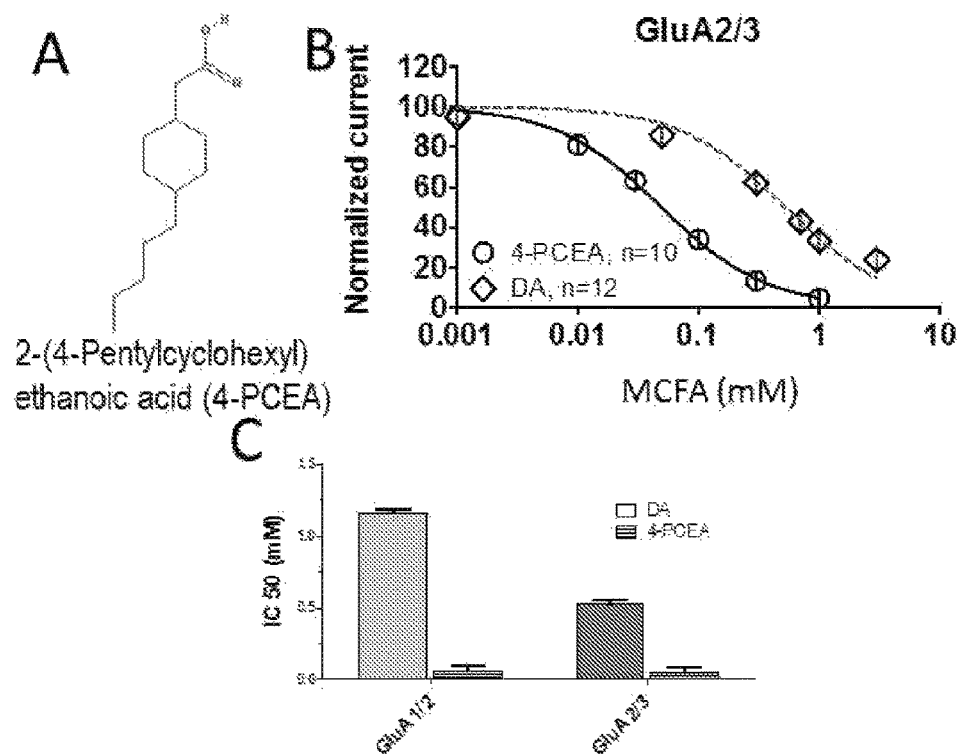
FIG. 2a shows the structure of 2-(4-pentylcyclohexyl) ethanoic acid (4-PCEA)
FIG. 2b shows the dose curve for two medium chain fatty acids (MCFA); 4-PCEA and decanoic acid (DA)
FIG. 2c is a graph showing the IC50 values for 4-PCEA and DA obtained from AMPA receptors of different subunit composition; GluR1/2 and GluR2/3.
Figure 3:
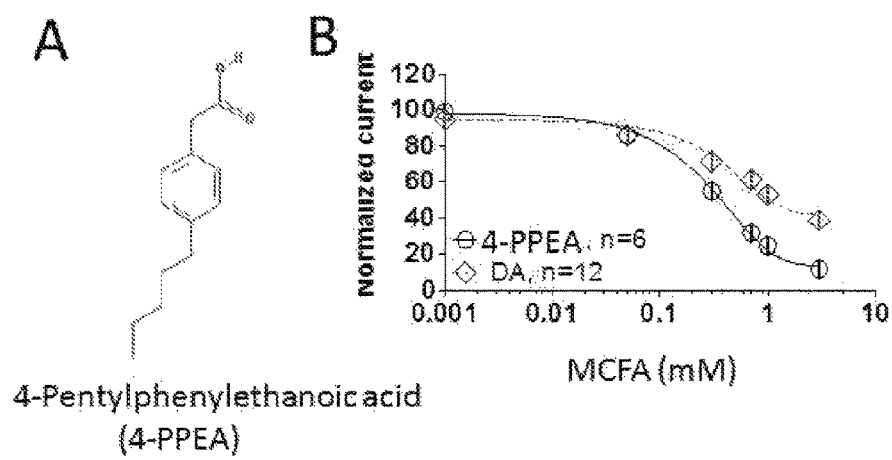
FIG. 3 shows the structure of 4-pentylphenylethanoic acid (4-PPEA) and the dose curve for two medium chain fatty acids (MCFA); 4-PPEA and decanoic acid (DA)

The inventors prepared the following compounds:
  trans-4-butylcyclohexane carboxylic acid (4-BCCA), the structure of which is shown in FIG. 1;
  4-butylbenzoic acid (4-BBA), as shown in FIG. 1;
  2-(4-pentylcyclohexyl)ethanoic acid (4-PCEA), as shown in FIG. 2; and
  4-pentylphenylethanoic acid (4-PPEA), as shown in FIG. 3.

In Vitro

The inventors show both trans-4-butylcyclohexane carboxylic acid (4-BCCA) and 4-butylbenzoic acid (4-BBA) provide comparable potency of AMPA receptors inhibition (as determined by IC50; in FIG. 1) to straight chain decanoic acid (DA) and branched fatty acid 4-ethyloctanoic acid (4-EOA) derivatives for potency in AMPA receptor mediated current using AMPA receptors expressed in oocytes. This inhibitory activity is greater than that shown for the straight chain nonanoic acid (NA), and much greater than octanoic acid (OA).

Additionally, the AMPA receptor inhibitory activity of 2-(4-pentylcyclohexyl)ethanoic acid (4-PCEA; FIG. 2A) was compared to decanoic acid (DA). FIG. 2B shows more potent inhibition of AMPA receptors (subunit GluA2/3) by 4-PCEA than decanoic acid. This enhanced inhibitory effect of 4-PCEA over decanoic acid is also seen with AMPA receptors consisting of GluA1/2 subunits shown in FIG. 2C. This shows that 4-PCEA is far more effective at inhibiting the AMPA receptor than DA.

Additionally, the AMPA receptor inhibitory activity of 2-(4-pentylphenyl)ethanoic acid (4-PPEA FIG. 3A) was compared to decanoic acid (DA). FIG. 3B shows more potent inhibition of AMPA receptors (subunit GluA2/3) by 4-PPEA than decanoic acid. This shows that 4-PPEA is far more effective at inhibiting the AMPA receptor than DA.

Figure 4:
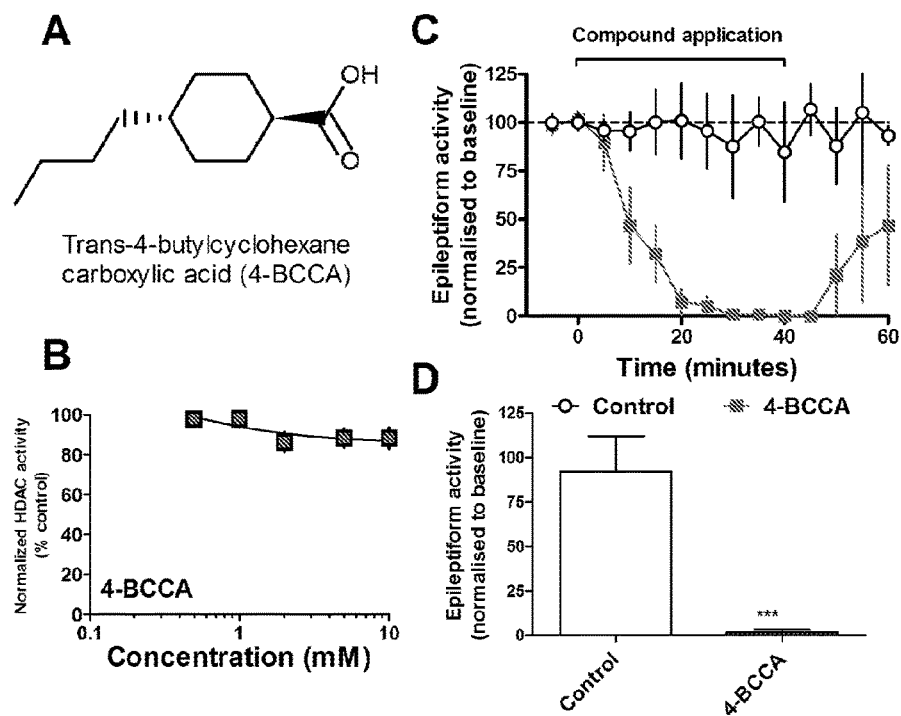
FIG. 4a shows the structure of trans-4-butylcyclohexane carboxylic acid (4-BCCA)
FIG. 4b is a graph showing quantification of a histone deacetylase (HDAC) inhibition assay employing human nuclear enzyme extracts (from HeLa cells) as the source of HDAC activity shown as fitted dose-response curves for 4-BCCA.
FIG. 4c is a graph showing the change in the frequency of PTZ-induced burst discharges in area CA1 recorded from the stratum pyramidal by application of 4-BCCA (n=5)
FIG. 4d is a graph showing the average epileptoform activity from 20-40 minute treatment of 4-BCCA.

The inventors then tested trans-4-butylcyclohexane carboxylic acid (4-BCCA) (FIG. 4A) using both the HDAC inhibitory assay (FIG. 4B) and the PTZ-induced hippocampal slice seizure model experiment (FIG. 4C). Analysis of 4-BCCA provided no HDAC inhibition with very strong epileptiform activity control (FIG. 4A,B,C; 1.7±1.5% of baseline, n=5). The complete block in seizure induction for this model suggests that 4-BCCA provides a possible lead candidate for developing improved epilepsy treatments.

In Vivo

The advantage of in vitro models is that efficacy is not dependent on the pharmacokinetics and blood-brain-barrier penetration of the compounds. However, these in vitro models of epileptiform activity may not necessarily predict in vivo efficacy both because of pharmacokinetics and also because these models do not monitor seizure activity in the whole brain. In the development of new anti-epileptics, in vivo models are therefore used both to better predict efficacy, and to provide evidence for physiochemical properties such as in vivo stability and blood brain barrier penetrance. The inventors therefore examined efficacy for 4-BCCA in multiple in vivo epilepsy models, in collaboration with the Anticonvulsant Screening Program (ASP), at the US National Institutes for Neurological Disorders and Stroke (NINDS). The results are shown in FIG. 5 then enabled a comparison with a widely used epilepsy treatment, valproic acid (VPA).

The inventors first employed a low frequency (6 Hz), long duration (3 s) corneal stimulation model because numerous second generation anti-epileptic drugs show poor seizure control in this assay (and so such a model may provide evidence of efficacy in drug resistant epilepsy). In this model, compounds are pre-administered to mice via i.p. injection and mice are challenged with sufficient current to elicit a psychomotor response (32 mA for 3 s) (Toman et al., 1952). The model causes forelimb clonus and then automatistic behavior characteristic of limbic epilepsy in humans. Our initial analysis of 4-BCCA showed an $ED_{50}$ of 81 mg/kg, indicating that 4-BCCA is more potent than valproic acid which has an $ED_{50}$ of 263 mg/kg in this model (Barton et al., 2001). 4-BCCA was then tested in three further in vivo seizure models. The maximal electric shock (MES) seizure model is one of the primary preclinical models used in epilepsy drug development (Barton et al., 2001). Using this model, 4-BCCA had $ED_{50}$ values of 100 mg/kg. The subcutaneous MET (scMET) model, thought to determine the seizure threshold for clonic seizures, showed that 4-BCCA showed an $EC_{50}$ value of ~150 mg/kg, whereas valproic acid had an equivalent effect at 191 mg/kg (Rowley and White, 2010). Finally, in the corneal kindled mouse model (CKM), that provides an in vivo model for temporal lobe epilepsy (White, 2003), 4-BCCA had an $EC_{50}$ value of 44 mg/kg, compared with valproic acid that shows equivalent activity at 174 mg/kg. This data strongly suggests enhanced activity of 4-BCCA over valproic acid in a range of distinct seizure models.

Discussion

The MCT ketogenic diet provides a widely used and effective treatment for drug resistant epilepsy in children, but is not employed for adult treatment due to lack of compliance.

The inventors have identified a novel chemical space providing enhanced seizure control activity over a widely used epilepsy treatment, valproic acid. This discovery was derived through their identification of an inhibitory effect of a medium chain fatty acid provided in the MCT ketogenic diet, decanoic acid, in directly inhibiting AMPA receptors. The novel family of cyclic compounds described here are related to but chemically distinct from decanoic acid, and provide a more potent AMPA receptor inhibitory activity than decanoic acid. These compounds therefore provided exciting new leads for further screening as epilepsy treatments.

The inventors also show that the lead candidate in this chemical space, 4-BCCA, is more effective than the widely used and effective epilepsy treatment valproic acid, in seizure control using an in vitro seizure model. In these experiments they show that following induction of seizure-like activity in rat hippocampal slices with the GABA(A) receptor antagonist, pentelenetetrazol (PTZ), 4-BCCA provides a 100% block in seizure activity, whereas valproic acid only provides a 23% reduction (Chang et al., 2013). This result suggests that the cyclic compounds outlined here provide potential new epilepsy treatments with enhanced activity over valproic acid.

The inventors next asked how the in vitro results in a much reduced system translate to the in vivo situation, which is more akin to human seizures and epilepsy. The inventors first employed the 6 Hz electric shock model (Barton et al., 2001), in which valproic acid, levetiracetam, phenytoin, lamotrigine, lacosamide, carisbamate, and retigabine have shown efficacy (Bialer et al., 2010). The enhanced potency of 4-BCCA over valproic acid in this model provides an encouraging step forward in developing new treatments in this chemical space. Since this compound also shows significantly decreased $ED_{50}$ values compared to valproic acid in the widely-used MES and scMET screening models and, importantly, in the corneal kindling model of temporal lobe epilepsy (Lothman and Williamson, 1994), this compound has significant potential as an anti-seizure drug.

The inventors have also examined effects of the lead compounds, 4-BCCA, on histone deacetylase (HDAC) activity. Direct inhibition of HDAC activity by valproic acid (Gottlicher et al., 2001; Gurvich et al., 2004) is thought to give rise to teratogenicity (Jentink et al., 2010; Koren et al., 2006), causing a variety of major and minor malformations, including neural tube defects, cleft lip and palate, cardiovascular abnormalities, genitourinary defects, developmental delay, endocrinological disorders, limb defects, and autism (Alsdorf and Wyszynski, 2005). This biochemical activity provides a crucial side effect profile to consider in the development of carboxylic acid-based anti-epileptic drugs. Structural requirements for this activity for valproic acid congeners suggest a critical role for branching of the parent compound on the second carbon of the fatty acid backbone (Bialer, 2010; Perucca, French and Bialer, 2007). The inventors show that 4-BCCA does not cause significant inhibitory effect upto 10 mM, whereas valproic acid has and IC50 of 2.3 mM against HDAC extract derived from a human cell line. This suggests that 4-BCCA, is unlikely to significantly inhibit HDAC activity, in vivo, at concentrations found in plasma for valproic acid (0.4-0.7 mM) (DSMV IV, 2000). This data also supports the enhanced safety of 4-BCCA in seizure control, showing a reduced potential for HDAC activity associated with teratogenicity.

The discovery of this new chemical space, comprising cyclic molecules, for seizure control also has implications for other therapeutic roles. The MCT diet provides a positive effect in decreasing brain excitability in young animals (de Almeida Rabello et al., 2008), as well as playing a neuroprotective role in traumatic brain injury and stroke (Gasior et al., 2006) suggesting the novel compounds may show efficacy against other neurological disorders characterized by neuronal cell death (Stafstrom and Rho, 2012), such as Alzheimer's disease (Reger et al., 2004; Henderson et al., 2009) and Parkinson's disease (VanItallie et al., 2005). In addition, since valproic acid is used in migraine and bipolar disorder prophylaxis, these new compounds may also show indications for these conditions (Lagace et al 2005) and stroke (Chen et al 2014). Future research into the use of these compounds for these conditions may provide important advances in therapy development.

EXAMPLE 2

Experimental Procedures
Compounds for Analysis

Fatty acids used in this study were: decanoic acid (DA), trans-4-butylcyclohexane carboxylic acid (4-BCCA) (TCI), a racemic mixture of both trans- and cis-2-(4-pentylcyclohexyl)ethanoic acid (4-PCEA), [4-(4-methylpentyl)cyclohexyl]acetic acid (#172), [4-(3-methylpentyl)cyclohexyl]acetic acid (#176), 4-(3-methylbutyl)cyclohexanecarboxylic acid (#181), 4-(2-methylbutyl)cyclohexanecarboxylic acid (#184), [4-(2-methylpentyl)cyclohexyl]acetic acid (#185), 4-[(1E)-but-1-en-1-yl]cyclohexanecarboxylic acid (#174), (4-pentylidenecyclohexyl)acetic acid (#182), 4-(propoxymethyl)cyclohexyl acetic acid (#175), 5-butylpiperidine-2-carboxylic acid (#178), {4-[(ethylamino)methyl]cyclohexyl}acetic acid (#179), 4-(ethoxymethyl)cyclohexancarboxylic acid (#177), and 4-propoxycyclohexanecarboxylic acid (#180). Compounds were prepared as 1000 times stocks (1 M) in dimethyl sulfoxide (DMSO). With the exception of 4-PCEA, stocks were dissolved in artificial cerebrospinal fluid (aCSF) or media to achieve their final experimental concentrations of 1 mM. The stock of 4-PCEA in DMSO was dissolved in artificial cerebrospinal fluid (aCSF) or media to achieve a final experimental concentration of 100 µM.

Oocyte Preparation and Injection

The procedure was as outlined in Example 1.

Activity of DA on GluA1/2 (shown as DA' in FIG. 9) was extrapolated from dose-response assays carried out in GluA1/2.

Discussion

The inventors obtained further compounds which fell within the chemical space they had identified above. Electrophysiology analysis of *Xenopus laevis* oocytes expressing GluA2/3 was then carried out on these compounds, and the results are shown in FIG. 8.

All of the compounds displayed inhibitory activity. In particular, some of the results show a strong inhibitory activity with a very low degree of error. All of the new compounds which were tested show a significant reduction of AMPA-R generated current in comparison to the control, with P<0.05 for compounds #175 and #177 (indicated by an "X" on FIG. 8) and P<0.001 for compounds #172, #174, #176, #178, #179, #180, #181, #182, #184 and #185 (indicated by an "XXX" on FIG. 8). Compounds #176, #181, #182, #184 and #185 all showed significant reduction of AMPA-R generated current in comparison to decanoic acid, with P<0.01 for compounds #181, #182 and #184 and P<0.001 for compounds #176 and #185. These compounds also showed significant reduction of AMPA-R generated current in comparison to 4-BCCA, with P<0.05 for compounds #181 and #184, P<0.01 for compound #182 and P<0.001 for compounds #176 and #185. P values provide a statistical assessment of the significance level of the data, where P values smaller than 0.05 indicate a significant effect, thus these compounds show a statistically relevant level of inhibition.

Electrophysiology analysis of *Xenopus laevis* oocytes expressing GluA1/2 was also carried out on compounds #184 and #185, and the results are shown in FIG. 9.

Both of these compounds show a significant reduction of AMPA-R generated current in comparison to decanoic acid, with P<0.001 for both compounds (indicated by an "***" on FIG. 9), thus these compounds show a statistically relevant level of inhibition.

Compounds #184 and #185 show particularly promising results. Both of these compounds comprise a tail group where the second carbon is substituted with a methyl group. It will be appreciated that spatially these compounds will be similar to bicyclic compounds comprising two fused six-membered rings. It is therefore hypothesised that bicyclic compounds would display similar inhibitory activity.

SUMMARY

In summary, a series of novel cyclic compounds were identified as targeting the same protein as a therapeutic medium chain fatty acid provided in the MCT ketogenic diet (decanoic acid). This target is a key receptor for an excitatory neurotransmitter glutamate, called AMPA receptors. These receptors provide a known target for seizure control (Rogawski 2011). The novel cyclic compounds were found to bind directly to AMPA receptors expressed in an oocyte model. Using an in vitro model of seizure-like activity a lead candidate from these compounds was shown to provide enhanced protection over, valproic acid, a widely used and effective epilepsy treatment. Given the remarkable value of the MCT diet in the treatment of epilepsies (Brandt et al., 2003; Huttenlocher et al., 1971; Neal et al., 2008; Neal et al., 2009; Sills et al., 1986), and its shortcomings in terms of adverse effects, there is interest in derivatives of medium chain fatty acids found in the MCT diet that will provide improved potency, pharmacokinetic or safety profiles. Since the MCT ketogenic diet has shown potential efficacy in other indications such as other seizure-related disorders, bipolar disorders, mania, migraine, Alzheimer's disease, Parkinson's disease or stroke, it is likely that these novel compounds will provide effective treatments for these conditions. The inventors clearly demonstrate that structurally specific cyclic compounds have more potent activity against AMPA receptors, and anti-seizure properties, whilst avoiding adverse side effect of HDAC inhibition, providing a new chemical space for the design of more potent and safer anti-epileptic treatments. The inventors also demonstrate that these compounds show enhanced in vivo seizure control potency over valproic acid suggesting these compounds will provide improved epilepsy treatments.

REFERENCE LIST

Lagace, D. C., W. T. O'Brien, N. Gurvich, M. W. Nachtigal, and P. S. Klein. 2005, Valproic acid: how it works. Or not. Clinical Neuroscience Research 4: 215-225.

Chen S[1], Wu H, Klebe D, Hong Y, Zhang J. Valproic Acid: A New Candidate of Therapeutic Application for the Acute Central Nervous System Injuries. *Neurochem Res.* 2014 Jan. 31. [Epub ahead of print]

Rogawski Michael A. Revisiting AMPA Receptors as an Antiepileptic Drug Target Epilepsy Currents, Vol. 11, No. 2 (March/April) 2011 pp. 56-63 de Almeida Rabello O M, da Rocha A T, de Oliveira S L, de Melo Lucena A L, de Lira C E, Soares A A, de Almeida C B and Ximenes-da-Silva A (2008) Effects of Short- Term and Long-Term Treatment With Medium- and Long-Chain Triglycerides Ketogenic Diet on Cortical Spreading Depression in Young Rats. Neurosci Lett 434: 66-70.

Armand V, Louvel J, Pumain R and Heinemann U (1998) Effects of New Valproate Derivatives on Epileptiform Discharges Induced by Pentylenetetrazole or Low $Mg^{2+}$ in Rat Entorhinal Cortex-Hippocampus Slices. Epilepsy Res 32:345-355.

Barton M E, Klein B D, Wolf H H and White H S (2001) Pharmacological Characterization of the 6 Hz Psychomotor Seizure Model of Partial Epilepsy. Epilepsy Res 47:217-227.

Bialer M, Johannessen S I, Levy R H, Perucca E, Tomson T and White H S (2010) Progress Report on New Antiepileptic Drugs: a Summary of the Tenth Eilat Conference (EILAT X). Epilepsy Res 92:89-124.

Bialer M and White H S (2010) Key Factors in the Discovery and Development of New Antiepileptic Drugs. Nat Rev Drug Discov 9:68-82.

Brandt C, Potschka H, Loscher W and Ebert U (2003)N-Methyl-D-Aspartate Receptor Blockade After Status Epilepticus Protects Against Limbic Brain Damage but Not Against Epilepsy in the Kainate Model of Temporal Lobe Epilepsy. Neuroscience 118:727-740.

Chang P and Walker M C (2011) Valproate Decreases Frequency Facilitation at Mossy Fiber—CA3 Synapses After Status Epilepticus. Epilepsy Res 93:192-196.

Davenport V D and Davenport H W (1948) The Relation Between Starvation, Metabolic Acidosis and Convulsive Seizures in Rats. J Nutr 36:139-151.

DeLorenzo R J, Sun D A and Deshpande L S (2005) Cellular Mechanisms Underlying Acquired Epilepsy: the Calcium Hypothesis of the Induction and Maintainance of Epilepsy. Pharmacol Ther 105:229-266.

Deshpande L S, Lou J K, Mian A, Blair R E, Sombati S, Attkisson E and DeLorenzo R J (2008) Time Course and Mechanism of Hippocampal Neuronal Death in an in Vitro Model of Status Epilepticus: Role of NMDA Receptor Activation and NMDA Dependent Calcium Entry. Eur J Pharmacol 583:73-83.

DSMV IV (2000) American Psychiatric Association: Diagnostic and Statistical Manual of Mental Disorders. American Psychiatric Association, Washington D.C.

Eikel D, Lampen A and Nau H (2006) Teratogenic Effects Mediated by Inhibition of Histone Deacetylases: Evidence From Quantitative Structure Activity Relationships of 20 Valproic Acid Derivatives. Chem Res Toxicol 19:272-278.

Gasior M, Rogawski M A and Hartman A L (2006) Neuroprotective and Disease-Modifying Effects of the Ketogenic Diet. Behav Pharmacol 17:431-439.

Gottlicher, M., S. Minucci, P. Zhu, O. H. Kramer, A. Schimpf, S. Giavara, J. P. Sleeman, C. F. Lo, C. Nervi, P. G. Pelicci, and T. Heinzel. 2001, Valproic acid defines a novel class of HDAC inhibitors inducing differentiation of transformed cells. EMBO J. 20: 6969-6978.

Gurvich, N., O. M. Tsygankova, J. L. Meinkoth, and P. S. Klein. 2004, Histone deacetylase is a target of valproic acid-mediated cellular differentiation. Cancer Res. 64: 1079-1086.

Huttenlocher P R, Wilbourn A J and Signore J M (1971) Medium-Chain Triglycerides As a Therapy for Intractable Childhood Epilepsy. Neurology 21:1097-1103.

Jentink J, Loane M A, Dolk H, Barisic I, Game E, Morris J K and de Jong-van den Berg L T (2010) Valproic Acid Monotherapy in Pregnancy and Major Congenital Malformations. N Engl J Med 362:2185-2193.

Koren, G., A. A. Nava-Ocampo, M. E. Moretti, R. Sussman, and I. Nulman. 2006, Major malformations with valproic acid. Can. Fam. Physician 52: 441-2, 444, 447.

Lothman E W and Williamson J M (1994) Closely Spaced Recurrent Hippocampal Seizures Elicit Two Types of Heightened Epileptogenesis: a Rapidly Developing, Transient Kindling and a Slowly Developing, Enduring Kindling. Brain Res 649:71-84.

Neal E G, Chaffe H, Schwartz R H, Lawson M S, Edwards N, Fitzsimmons G, Whitney A and Cross J H (2008) The Ketogenic Diet for the Treatment of Childhood Epilepsy: a Randomised Controlled Trial. Lancet Neurol 7:500-506.

Neal E G, Chaffe H, Schwartz R H, Lawson M S, Edwards N, Fitzsimmons G, Whitney A and Cross J H (2009) A Randomized Trial of Classical and Medium-Chain Triglyceride Ketogenic Diets in the Treatment of Childhood Epilepsy. Epilepsia 50:1109-1117.

Perucca E, French J and Bialer M (2007) Development of New Antiepileptic Drugs: Challenges, Incentives, and Recent Advances. Lancet Neurol 6:793-804.

Petty W C and Karler R (1965) The Influence of Aging on the Activity of Anticonvulsant Drugs. J Pharmacol Exp Ther 150:443-448.

Phiel C J, Zhang F, Huang E Y, Guenther M G, Lazar M A and Klein P S (2001) Histone Deacetylase Is a Direct Target of Valproic Acid, a Potent Anticonvulsant, Mood Stabilizer, and Teratogen. J Biol Chem 276:36734-36741.

R. J. Racine, J. G. Gartner, and W. M. Burnham, Epileptiform activity and neural plasticity in limbic structures. Brain Res. 47, 262-268 (1972)

Reger M A, Henderson S T, Hale C, Cholerton B, Baker L D, Watson G S, Hyde K, Chapman D and Craft S (2004) Effects of Beta-Hydroxybutyrate on Cognition in Memory-Impaired Adults. Neurobiol Aging 25:311-314.

Rowley N M and White H S (2010) Comparative Anticonvulsant Efficacy in the Corneal Kindled Mouse Model of Partial Epilepsy: Correlation With Other Seizure and Epilepsy Models. Epilepsy Res 92:163-169.

Sills M A, Forsythe W I, Haidukewych D, MacDonald A and Robinson M (1986) The Medium Chain Triglyceride Diet and Intractable Epilepsy. Arch Dis Child 61:1168-1172.

Stafstrom C E and Rho J M (2012) The Ketogenic Diet As a Treatment Paradigm for Diverse Neurological Disorders. Front Pharmacol 3:59.

Swinyard E A, Woodhead J H, Wolf H H and Kupferberg H J (1995) General principles: experimental selection, quantification, and evaluation of anticonvulsants, in Antiepileptic Drugs (Levy L A, Meldrum B, Penry J K and Dreifuss F E eds) pp 85-102, Raven Press, New York.

Teratogenicity of sodium valproate. Alsdorf R, Wyszynski D F. Expert Opin Drug Saf. 2005 March; 4(2):345-53. Review.

Toman J E, Everett G M and Richards R K (1952) The Search for New Drugs Against Epilepsy. Tex Rep Biol Med 10:96-104.

VanItallie T B, Nonas C, Di R A, Boyar K, Hyams K and Heymsfield S B (2005) Treatment of Parkinson Disease With Diet-Induced Hyperketonemia: a Feasibility Study. Neurology 64:728-730.

White H S (2003) Preclinical Development of Antiepileptic Drugs: Past, Present, and Future Directions. Epilepsia 44 Suppl 7:2-8.

White H S, Smith M D and Wilcox K S (2007) Mechanisms of Action of Antiepileptic Drugs. Int Rev Neurobiol 81:85-110.

White H S, Woodhead J H and Franklin M R (1995) General principles; experimental selection, quantification and evaluation of antiepileptic drugs, in Antiepileptic Drugs (Levy R H and Meldrugm B S eds) pp 99-110, Raven Press, New York.

Woolley D E, Timiras P S, Rosenzweig M R, Krech D and Bennett E L (1961) Sex and Strain Differences in Electroshock Convulsions of the Rat. Nature 190:515-516.

The invention claimed is:

1. A method of treating or ameliorating a seizure-related disorder, the method comprising administering, to a subject in need of such treatment, a therapeutically effective amount of a compound selected from the group consisting of:

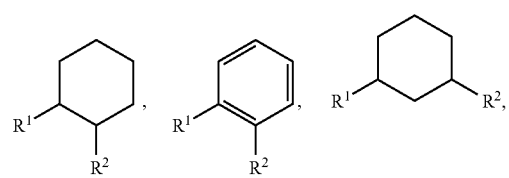

-continued

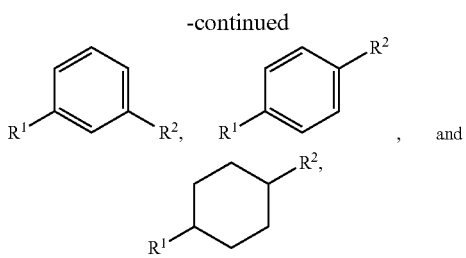

wherein:
R¹ is —COOH or -alkyl-COOH; and
R² is a straight or branched alkyl or alkenyl group with 1 to 20 C atoms, and wherein the backbone of the alkyl or alkenyl group is optionally interrupted by one or more heteroatoms, or a pharmaceutically acceptable salt or solvate thereof.

2. The method of claim 1, wherein R¹ is a —COOH or -alkyl-COOH group with 1 to 5 carbon atoms.

3. The method of claim 1, wherein R¹ comprises —COOH or —CH₂—COOH.

4. The method of claim 1, wherein the compound comprises a compound of formula:

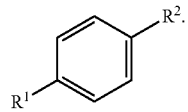

5. The method of claim 1, wherein the compound comprises a compound of formula:

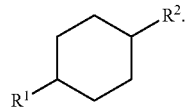

6. The method of claim 1, wherein R² is an alkyl or alkenyl group with a backbone comprising 2 to 15 C atoms.

7. The method of claim 1, wherein R² comprises a C₄₋₅ alkyl group.

8. The method of claim 6, wherein the backbone of the R² group is substituted with a C₁₋₄ alkyl group.

9. The method of claim 1, wherein R² comprises one or more unsaturated bonds.

10. The method of claim 1, wherein the backbone of the alkyl or alkenyl group is interrupted by one or more heteroatoms.

11. The method of claim 1, wherein the compound is cis-2-(4-butylcyclohexyl)ethanoic acid, trans-2-(4-butylcyclohexyl)ethanoic acid, cis-2-(4-pentylcyclohexyl)ethanoic acid, trans-2-(4-pentylcyclohexyl)ethanoic acid, 2-(4-butylphenyl)ethanoic acid, 2-(4-pentylphenyl)ethanoic acid, cis-4-butylcyclohexanecarboxylic acid, trans-4-butylcyclohexanecarboxylic acid, cis-4-pentylcyclohexanecarboxylic acid, trans-4-pentylcyclohexanecarboxylic acid, 4-butylbenzoic acid, 4-pentylbenzoic acid, cis-[4-(4-methylpentyl)cyclohexyl]acetic acid, trans-[4-(4-methylpentyl)cyclohexyl]acetic acid, cis-[4-(3-methylpentyl)cyclohexyl]acetic acid, trans-[4-(3-methylpentyl)cyclohexyl]acetic acid, cis-4-(3-methylbutyl)cyclohexanecarboxylic acid, trans-4-(3-methylbutyl)cyclohexanecarboxylic acid, cis-4-(2- methylbutyl)cyclohexanecarboxylic acid, trans-4-(2-methylbutyl)cyclohexanecarboxylic acid, cis-[4-2-methylpentyl)cyclohexyl]acetic acid, trans-[4-(2-methylpentyl)cyclohexyl]acetic acid, cis-4-[(1E)-but-1-en-1-yl]cyclohexanecarboxylic acid, trans-4-[(1E)-but-1-en-1-yl]cyclohexanecarboxylic acid, cis-(4-pentylidenecyclohexyl)acetic acid, trans-(4-pentylidenecyclohexyl)acetic acid, cis-4-(propoxymethyl)cyclohexyl acetic acid, trans-4-(propoxymethyl)cyclohexyl acetic acid, cis-{4-[(ethylamino)methyl]cyclohexyl}acetic acid, trans-{4-[(ethylamino)methyl]cyclohexyl}acetic acid, cis-4-(ethoxymethyl)cyclohexancarboxylic acid, trans-4-(ethoxymethyl)cyclohexancarboxylic acid, cis-4-propoxycyclohexanecarboxylic acid, or trans-4-propoxycyclohexanecarboxylic acid.

12. The method of claim 1, wherein the compound is [4-(4-methylpentyl)cyclohexyl]acetic acid; [4-(3-methylpentyl)cyclohexyl]acetic acid; 4-(3-methylbutyl)cyclohexanecarboxylic acid; (4-pentylidenecyclohexyl)acetic acid; 4-(2-methylbutyl)cyclohexanecarboxylic acid; or [4-(2-methylpentyl)cyclohexyl]acetic acid.

13. The method of claim 1, wherein the compound is:

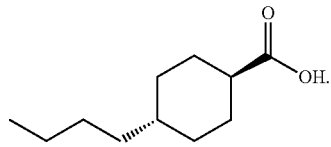

* * * * *